(12) United States Patent
McCormick et al.

(10) Patent No.: US 7,186,786 B2
(45) Date of Patent: Mar. 6, 2007

(54) CHAIN TRANSFER AGENTS FOR RAFT POLYMERIZATION IN AQUEOUS MEDIA

(75) Inventors: Charles L. McCormick, Hattiesburg, MS (US); Michael S. Donovan, Hattiesburg, MS (US); Andrew B. Lowe, Hattiesburg, MS (US); Brent S. Sumerlin, Hattiesburg, MS (US); David B. Thomas, Hattiesburg, MS (US)

(73) Assignee: University of Southern Mississippi, Hattiesburg, MS (US)

( * ) Notice: Subject to any disclaimer, the term of this patent is extended or adjusted under 35 U.S.C. 154(b) by 59 days.

(21) Appl. No.: 11/057,762

(22) Filed: Feb. 14, 2005

(65) Prior Publication Data

US 2006/0111532 A1 May 25, 2006

Related U.S. Application Data

(60) Division of application No. 10/337,225, filed on Jan. 6, 2003, now Pat. No. 6,855,840, which is a continuation-in-part of application No. 10/073,820, filed on Feb. 11, 2002, now abandoned.

(51) Int. Cl.
C08L 33/26 (2006.01)

(52) U.S. Cl. .............. 526/222; 526/193; 526/217; 526/220; 526/225; 524/555

(58) Field of Classification Search ................ 526/193, 526/217, 220, 222, 225, 303.1; 524/555
See application file for complete search history.

(56) References Cited

U.S. PATENT DOCUMENTS

| 6,380,335 B1 | 4/2002 | Charmot et al. |
| 6,642,318 B1 | 11/2003 | Chiefari et al. |
| 6,765,076 B2 | 7/2004 | Benicewicz et al. |
| 2002/0198347 A1 | 12/2002 | Adam et al. |

FOREIGN PATENT DOCUMENTS

| FR | 2794463 | 12/2000 |
| WO | WO 98/01478 | 1/1998 |
| WO | WO 98/58974 | 12/1998 |
| WO | WO 99/05099 | 2/1999 |
| WO | WO 99/31144 | 6/1999 |
| WO | WO 99/35177 | 7/1999 |

OTHER PUBLICATIONS

Atkinson, E.R., et al., "Potential Antiradiation Drugs, I.Amide, Hydroxamic Acid, and Hydrazine Derivatives of Mercapto Acides, Amino Thioacides," *J. Med. Chem.*, 8(1):29-33 (1965).

Barner-Kowollik, C., et al., "Kinetic Investigations of Reversible Additional Fragmentation Chain Transfer Polymerizations: Cumyl Phenyldithioacetate Mediated Homopolymerizations of Styrene and Methyl Methacrylate," *Macromolecules*, 34:7849-7857 (2001).

Bhandari, C.S., et al., Preparation and Electornic Spectra of Mercaptoacetamides, *J. fur praktische Chemie*, 313(5):849-854 (1971).

Chiefari, J., et al., "Living Free-Radical Polymerization by Reversible Addition-Fragmentation Chain Transfer: The RAFT Process," *Macromolecules*, 31:5559-5562 (1998).

De Brouwer, H., et al., "Living Radical Polymerization in Miniemulsion Using Reversible Addition-Fregmentation Chain Transfer," *Macromolecules*, 33:9239-9246 (2000).

Donovan, M.S., et al., "Investigation of the Effects of Chain Transfer Agent Architecture on the Synthesis of Near Monodisperse Poly (N,N-Dimethylacrylamide) Via RAFT," *Polym. Preprints*, 42(2):405-406(2001).

Donovan M.S., et al., "Synthesis of Well-Defined, Stimuli-Responsive, Water-Soluble Polymers via the RAFT Process," *Polym. Preprints*, 40(2):281-282 (1999).

Mitsukami, Y., et al., "Water-Soluble Polymers, 81. Direct Synthesis of Hydrophilic Styrenic-Bazsed Homopolymers and Block Copolymers in Aqueous Solution via RAFT," *Macromolecules*, 34:2248-2256 (2001).

Moad, G., et al., "Living Free-Radical Polymerization with Reversible Addition-Fragmentation Chain Transfer (The Life of RAFT)," *Polym. Int.*, 49:993-1001 (2000).

Moad, G. and Solomon, H.D., *The Chemistry of Free Radical Polymerization* (London:Pergamon), pp. 53-95 (1995).

Sumerlin, B.S., et al., "Water Soluble Polymers, 84. Controlled Polymerization in Aueous Media of Anionic Acrylamide Monomers via RAFT," *Macromolecules*, 34:6561-6564 (2001).

Taton, D., et al., "Direct Synthesis of Double Hydrophilic Statistical Di-and Triblock Copolymers Comprised of Acrylamide and Acrylic Acid Units via the MADIX Process," *Macromol. Rapid Commun.*, 22:1497-1503 (2001).

*Primary Examiner*—Helen L. Pezzuto
(74) *Attorney, Agent, or Firm*—Howrey LLP

(57) ABSTRACT

Polymers and copolymers synthesized by means that yield a narrow range of molecular weights can have different properties than polymers synthesized by conventional means. In order to obtain such polymers, however, polymerization must be controlled. One type of controlled polymerization is the reversible addition-fragmentation chain transfer (RAFT) process, which has characteristics of a living polymerization. The present invention discloses a group of dithioesters and trithioesters suitable as chain transfer agents for RAFT polymerization. The present invention also discloses RAFT polymerizations conducted in aqueous media.

10 Claims, 9 Drawing Sheets

Figure 1A
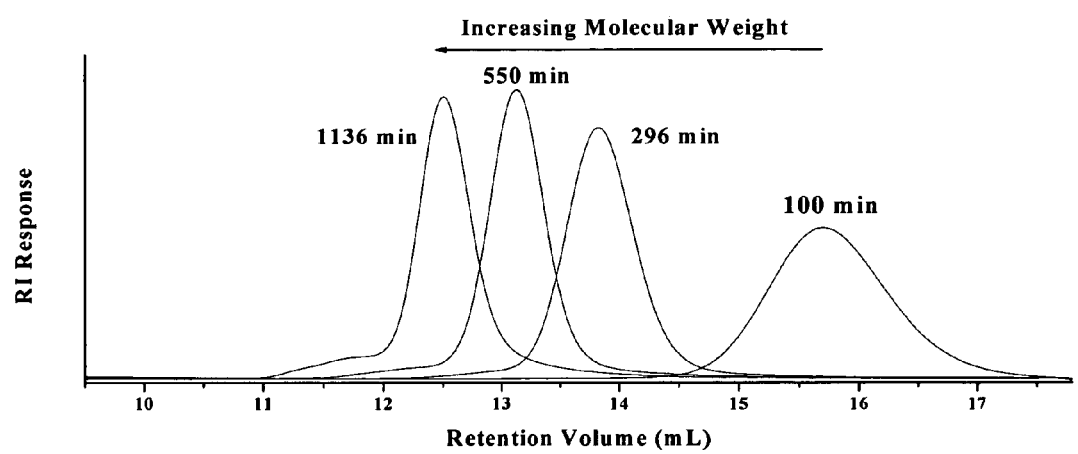
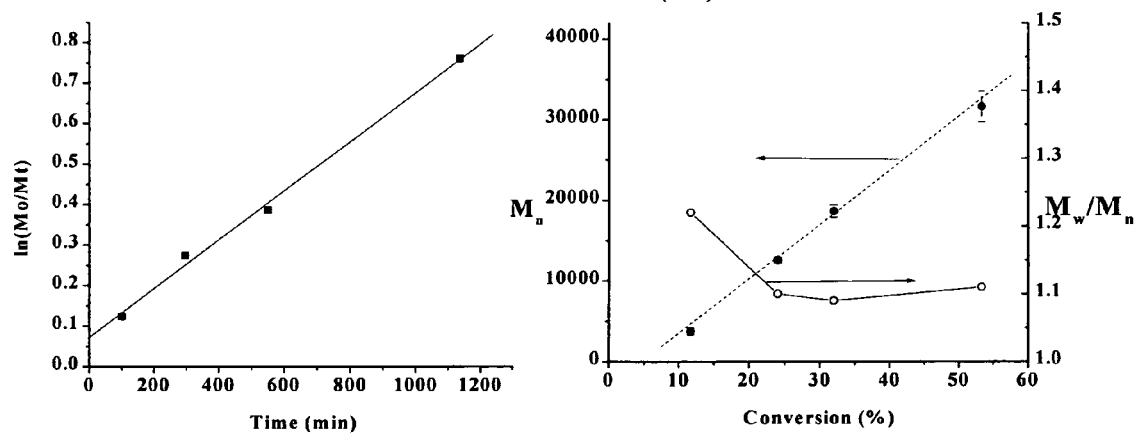
Figure 1B
Figure 1C

Figure 3A
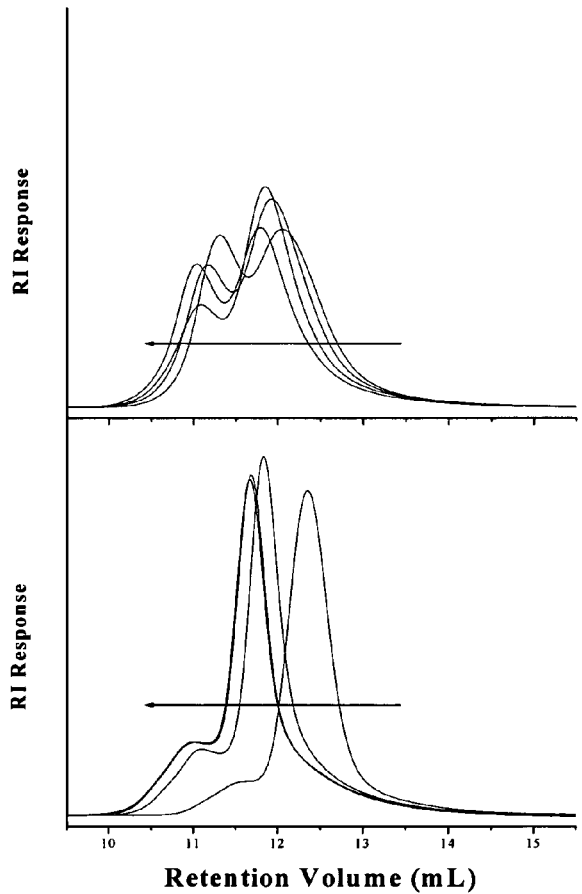
Figure 3B
Figure 3C
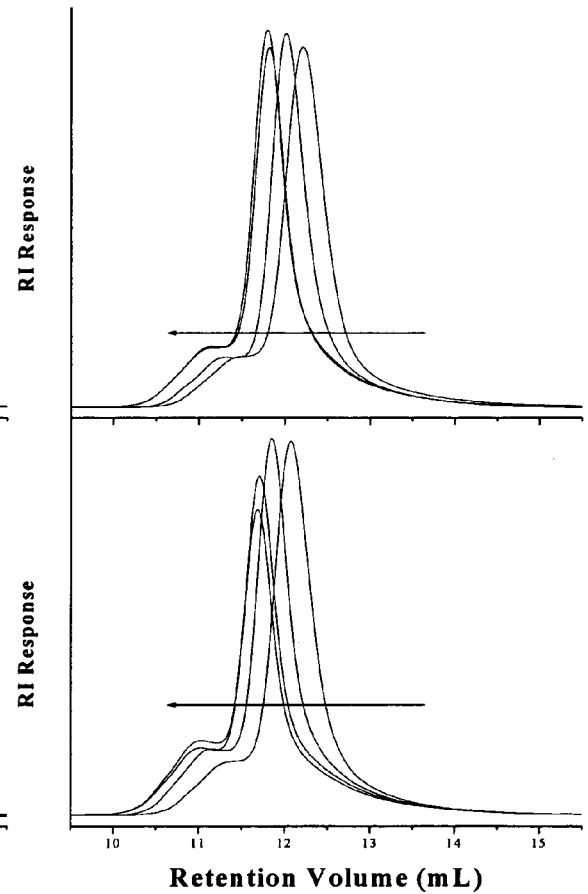
Figure 3D

CHAIN TRANSFER AGENTS FOR RAFT POLYMERIZATION IN AQUEOUS MEDIA

RELATED APPLICATION

This application is a divisional of U.S. application Ser. No. 10/337,225 filed Jan. 6, 2003, now U.S. Pat. No. 6,855,840 which is a continuation-in-part of U.S. application Ser. No. 10/073,820 filed Feb. 11, 2002, now abandoned the entire teachings which are incorporated herein by reference.

BACKGROUND OF THE INVENTION

In a polymer or copolymer synthesis, achieving a product with a desired molecular weight and a narrow weight distribution, or polydispersity, requires a controlled process. Polymers with a narrow molecular weight distribution can exhibit substantially different behavior and properties than polymers prepared by conventional means. Living polymerizations provide the maximum degree of control for the synthesis of polymers with predictable well-defined structures. The characteristics of a living polymerization include: polymerization proceeding until all monomer is consumed, number average molecular weight as a linear function of conversion, molecular weight control by the stoichiometry of the reaction, and block copolymer preparation by sequential monomer addition.

It has been stated that living polymerization to give polymers of low molecular weight distribution requires the absence of chain transfer and termination reactions. In a living polymerization, the only "allowed" elementary reactions are initiation and propagation, which take place uniformly with respect to all growing polymer chains. However, it has also been shown that if the chain transfer process is reversible, polymerization can still possess most of the characteristics of living polymerization.

It has been found that the reversible addition-fragmentation chain transfer (RAFT) process suppresses termination reactions through the addition of a suitable thiocarbonylthio compound, also known as a dithioester, to an otherwise conventional free radical polymerization. Control in such a RAFT process is thought to be achieved through a degenerative chain transfer mechanism in which a propagating radical reacts with the thiocarbonylthio compound to produce an intermediate radical species. This process decreases the number of free radicals available for termination reactions that require two free radicals.

Although RAFT polymerizations have been demonstrated to work under a variety of conditions, further research is required to demonstrate the effectiveness of RAFT polymerizations in aqueous solvent systems. Specifically, there is a need to develop dithioester chain transfer agents that are both soluble and stable in water. Also, there is a need to develop dithioesters that are tailored to the monomer being polymerized.

SUMMARY OF THE INVENTION

It has been found that a large group of compounds comprising a dithioester moiety act as excellent chain transfer agents in the RAFT process of producing polymers. It has further been found that many of these dithioesters and trithioesters, under the proper conditions, are stable towards hydrolysis in water and can be used in this medium to control free radical polymerizations. In addition, it has been found that a dithioester, particularly a water-soluble dithioester, with electronic and/or structural similarities to the monomer being polymerized is particularly desirable. These dithioesters are able to polymerize a wide range of related monomers in water to yield water-soluble polymers of controlled molecular weight, molecular weight distribution, and tailored architectures.

In one embodiment, the present invention is a group of dithioesters and trithioesters represented by the structural formula:

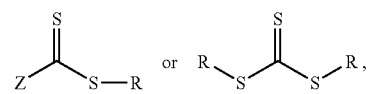

where Z in the dithioesters comprises an alkoxy group, a group represented by the structural formula:

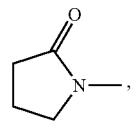

or one or more aromatic or heteroaromatic groups optionally substituted by one or more hydrophilic functional groups with optionally an ether or alkylene linkage between said aromatic- or heteroaromatic-containing group and the dithioester moiety; and R comprises a group represented by the structural formula:

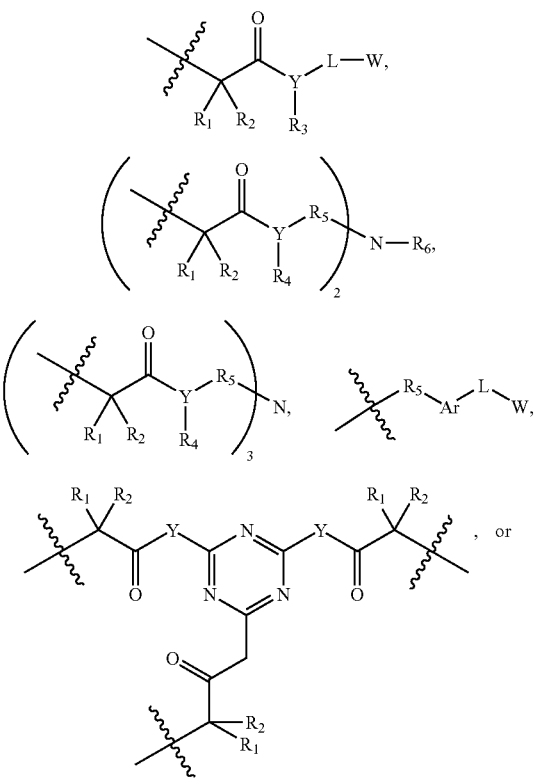

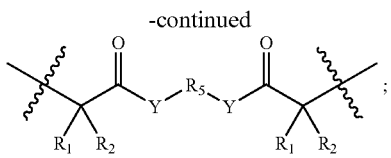

where Ar is an aromatic or heteroaromatic group; L is a bond, an C1–C20 azaalkylene group, or a C1–C20 straight-chained or branched alkylene group; $R_1$ and $R_2$ are each independently hydrogen, a C1–C10 alkyl group, or a cyano group; $R_3$ and $R_4$ are each independently hydrogen or a C1–C10 alkyl group when Y is N or C, and are each lone electron pairs when Y is O; $R_5$ is a bond or a branched or straight-chained C1–C10 alkylene group; $R_6$ is hydrogen or a C1–C10 alkyl group; W is selected from the group consisting of —H, —$SO_3^-M^+$, —COOH, —$COO^-M^+$, —$NH_2$, —$NR'_2$, —NR'H, —$NR'_3{}^+X^-$, —$PO_4^-M^+$, —OH, —$(—OCH_2CH_2—)_xR'$, —$(—CH_2CH_2O—)_xR'$, —$CONH_2$, —CONHR', —$CONR'_2$, —$NR'(CH_2)_xCOO^-M^+$, —$NR'(CH_2)_xOPO_3^-M^+$, —$NR'(CH_2)_xSO_3^-M^+$, —$N^+R'_2(CH_2)_xCOO^-M^+$, —$N^+R'_2(CH_2)_xOPO_3^-M^+$, —$N^+R'_2(CH_2)_xSO_3^-M^+$, —SCN, naphthyl, and dansyl; $M^+$ is ammonia, an ammonium ion, an alkali metal ion, an alkaline earth metal ion, or hydronium; R' is independently hydrogen or an alkyl group; x is an integer from 1 to about 20; $X^-$ is a halide, sulfate, phosphate, carboxylate, or sulfonate; and Y is selected from the group consisting of N, O, and C.

In a preferred embodiment, $R_1$ and $R_2$ are each independently hydrogen or a methyl group.

In another embodiment, the present invention is a method of preparing a polymer or copolymer, comprising reacting a polymerizable monomer or co-monomer, a dithioester or trithioester of the present invention, and free radicals produced by a free radical source in a solvent. Preferably, the solvent is water and optionally a water-miscible organic solvent such as dimethylformamide. Even more preferably, the solvent is water. When polymerizing monomers or comonomers having an acrylamide moiety, the pH of the solvent (e.g., water) is advantageously acidic, for example, where the pH is greater than about 2 and less than about 6.5 or in some instances, greater than about 4 and less than about 6, or in more particular instances, greater than about 4.5 and less than about 5.5.

The present invention has many advantages. Dithioesters and trithioesters of the present invention are capable of controlling a polymerization, such that the molecular weight of the polymers can be regulated and the molecular weight distribution is within a narrow range. Dithioesters of the present invention are also largely soluble in water and undergo slow hydrolysis. When controlled (RAFT) polymerizations are carried out with these dithioesters, the polymerization can be conducted in water, largely or entirely eliminating the need for and cost of organic solvents.

BRIEF DESCRIPTION OF THE DRAWINGS

FIG. 1A–FIG. 1C shows (A) size exclusion chromatograms (SEC) for PDMA with chain transfer agent (CTA) N,N-dimethyl-s-thiobenzoylthiopropionamide (1c) (target MW=40,000) in $d_6$-benzene at 60° C. using a CTA/initiator (I) ratio of 5/1, [monomer]=1.95 M, [CTA]=4.27×10⁻³, [I]=8.46×10⁻⁴, (B) plot of ln $(M_o/M_t)$ as a function of polymerization time, and (C) evolution of number average number weight and polydispersity $(M_w/M_n)$ with conversion.

FIG. 3A–FIG. 3D shows SEC traces for DMA polymerizations using CTA/I of 5/1 for CTA 1a–1d in $C_6D_6$ (60° C.) at extended polymerization times.

DETAILED DESCRIPTION OF THE INVENTION

Figure 2:
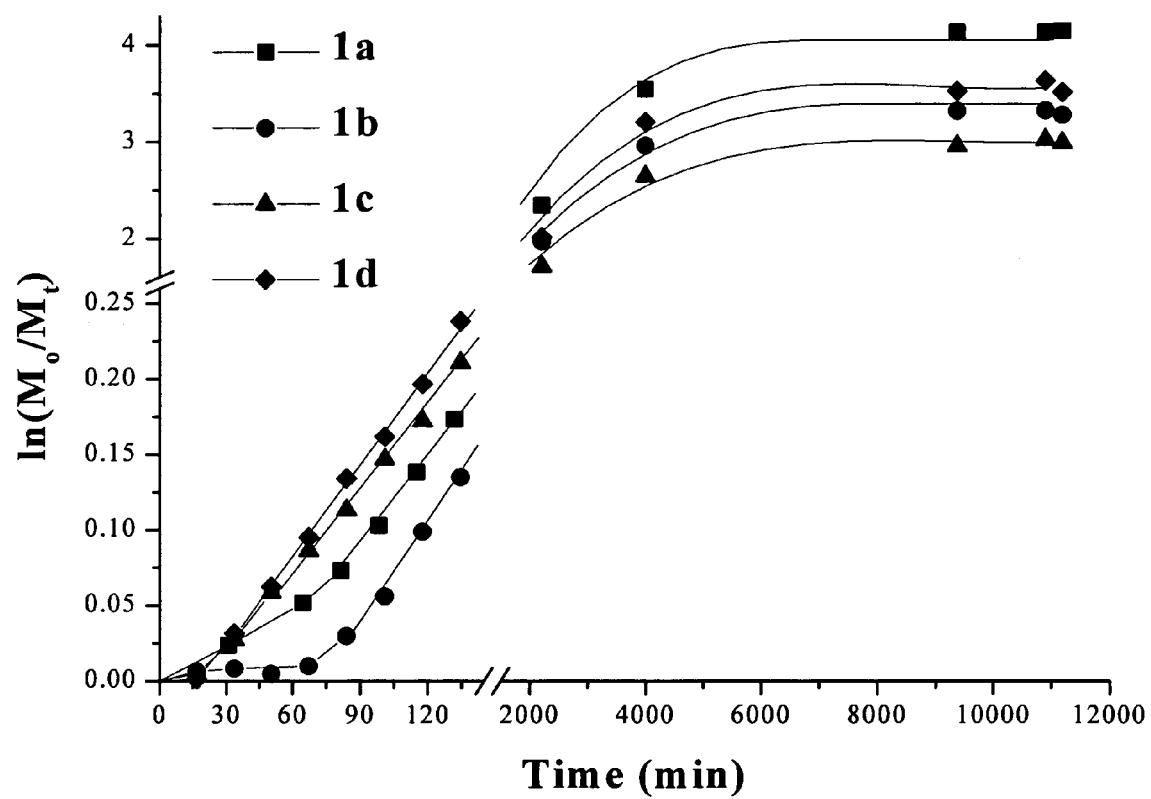
FIG. 2 shows plots of ln $(MW_o MW_t)$ versus time for N,N-dimethylacrylamide (DMA) polymerizations in an NMR spectrometer in $C_6D_6$ (60° C.) using CTAs 1a–1d.

A useful and efficient process for producing polymers and copolymers from monomers is the carrying out of a reversible addition-fragmentation chain transfer (RAFT) procedure with dithioesters or trithioesters as chain transfer agents (CTA's). The dithioester and trithioester chain transfer agents of the present invention are particularly advantageous. They can be used to produce polymers with low polydispersities. Many of the dithioester CTA's of the present invention can be used to produce a variety of polymers by the RAFT procedure in aqueous media.

The dithioesters and trithioesters of the present invention can be represented by the structural formula:

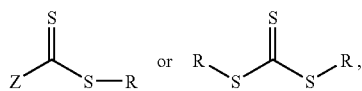

In this structural formula, Z comprises an alkoxy group, a group represented by the structural formula:

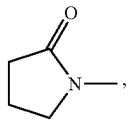

or one or more aromatic or heteroaromatic groups optionally substituted by one or more hydrophilic functional groups with optionally an ether or alkylene linkage between said aromatic- or heteroaromatic-containing group and the dithioester moiety. R comprises a group represented by the structural formula:

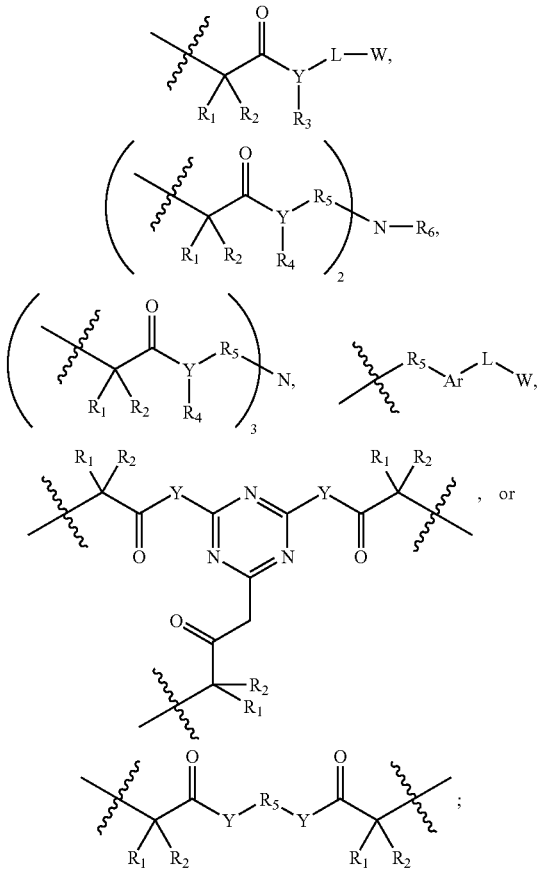

where Ar is an aromatic or heteroaromatic group; L is a bond, an C1–C20 azaalkylene group, or a C1–C20 straight-chained or branched alkylene group; $R_1$ and $R_2$ are each independently hydrogen, a C1–C10 alkyl group, or a cyano group; $R_3$ and $R_4$ are each independently hydrogen or a C1–C10 alkyl group when Y is N or C, and are each lone electron pairs when Y is O; $R_5$ is a bond or a branched or straight-chained C1–C10 alkylene group; $R_6$ is hydrogen or a C1–C10 alkyl group; W is selected from the group consisting of —H, —$SO_3^-M^+$, —COOH, —$COO^-M^+$, —$NH_2$, —$NR'_2$, —NR'H, —$NR'_3{}^+X^-$, —$PO_4^-M^+$, —OH, —(—$OCH_2CH_2$—)$_x$R', —(—$CH_2CH_2O$—)$_x$R', —$CONH_2$, —CONHR', —$CONR'_2$, —NR'($CH_2$)$_x$$COO^-M^+$, —NR'($CH_2$)$_x$$OPO_3^-M^+$, —NR'($CH_2$)$_x$$SO_3^-M^+$, —$N^+R'_2$($CH_2$)$_x$ $COO^-M^+$, —$N^+R'_2$($CH_2$)$_x$$OPO_3^-M^+$, and —$N^+R'_2$($CH_2$)$_x$ $SO_3^-M^+$, naphthyl, and dansyl; $M^+$ is ammonia, an ammonium ion, an alkali metal ion, an alkaline earth metal ion, or hydronium; R' is independently hydrogen or an alkyl group; x is an integer from 1 to about 20; $X^-$ is a halide, sulfate, phosphate, carboxylate, or sulfonate; and Y is selected from the group consisting of N, O, and C.

R and Z groups of the present invention are preferably substituted by one or more hydrophilic functional groups. These hydrophilic functional groups include $SO_3^-M^+$, —COOH, —$COO^-M^+$, —$NH_2$, —$NR'_2$, —NR'H, —$NR'_3{}^+$ $X^-$, —$PO_4^-M^+$, —OH, —(—$OCH_2CH_2$—)$_x$H, —$CONH_2$, —CONHR', —$CONR'_2$, —NR'($CH_2$)$_x$$COO^-M^+$, —NR' ($CH_2$)$_x$$OPO_3^-M^+$, —NR' ($CH_2$)$_x$$SO_3^-M^+$, —$N^+R'_2$($CH_2$)$_x$ $COO^-M^+$, —$N^+R'_2$($CH_2$)$_x$$OPO_3^-M^+$, —$N^+R'_2$($CH_2$)$_x$$SO_3^-$ $M^+$, or a combination thereof; and $M^+$, R', x, and $X^-$ are as previously defined.

Preferred Z groups of the present invention comprise a phenyl, benzyl, pyrrole, indole, isoindole, or ethoxy group. Especially preferred Z groups are represented by structural formulae:

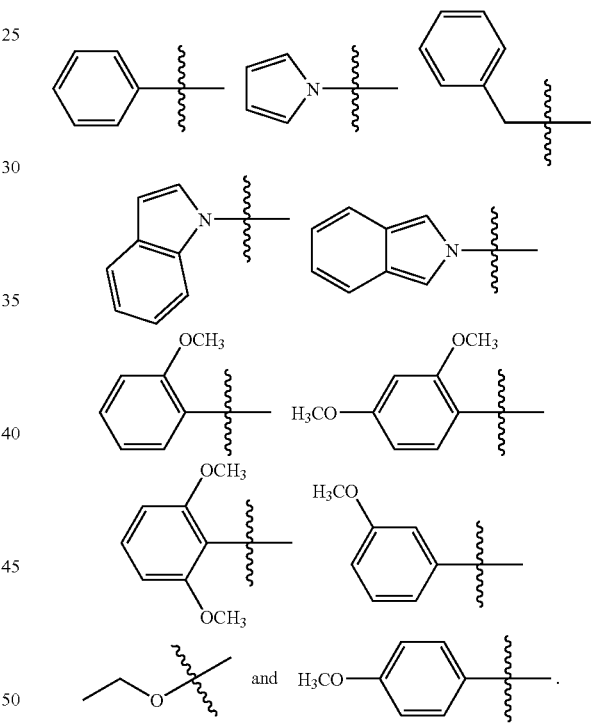

Preferred R groups are represented by the structural formulae:

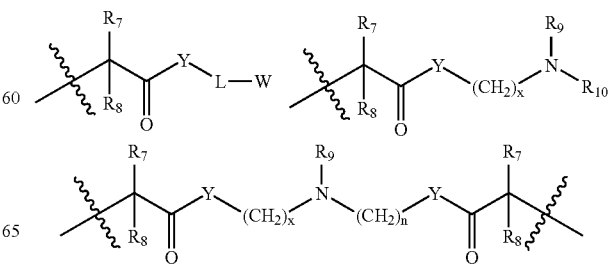

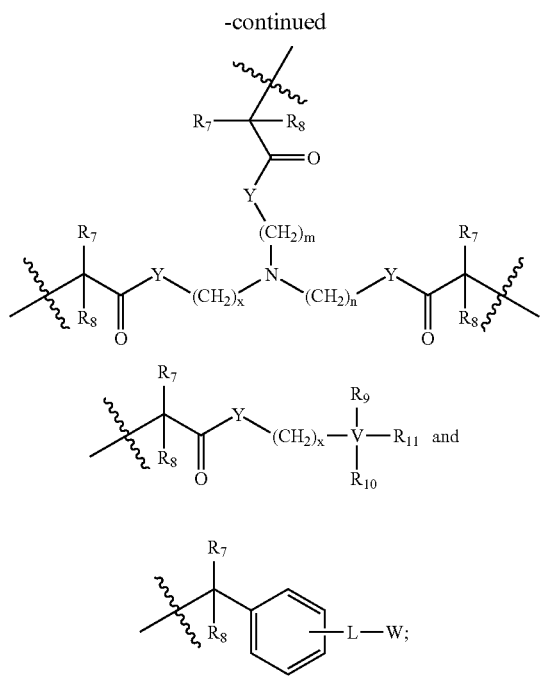

where m and n are each integers from 1 to about 10; $R_7$, $R_8$, $R_9$, $R_{10}$, and $R_{11}$ are each independently hydrogen or a C1–10 alkyl group; L, $M^+$, R', W, $X^-$, x, and Y are as previously defined; and V is selected from the group consisting of C and N. Preferably, $R_7$ and $R_8$ are each independently hydrogen or a methyl group.

Especially preferred R groups of the present invention are represented by the structural formulae:

where $M^+$, $X^-$ as previously defined.

Additional suitable R groups of the present invention are represented by the structural formulae:

-continued
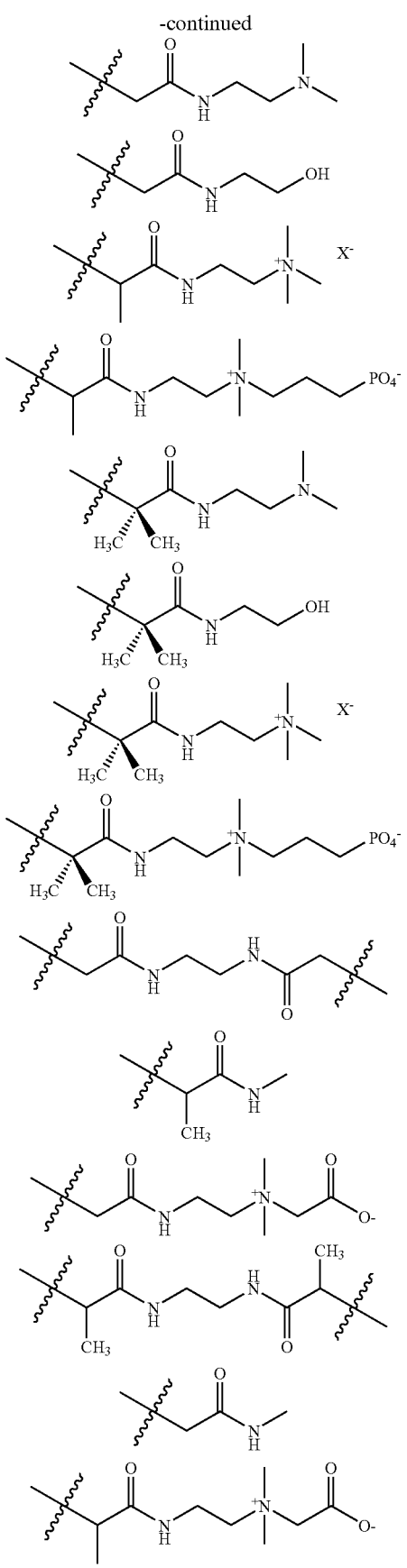
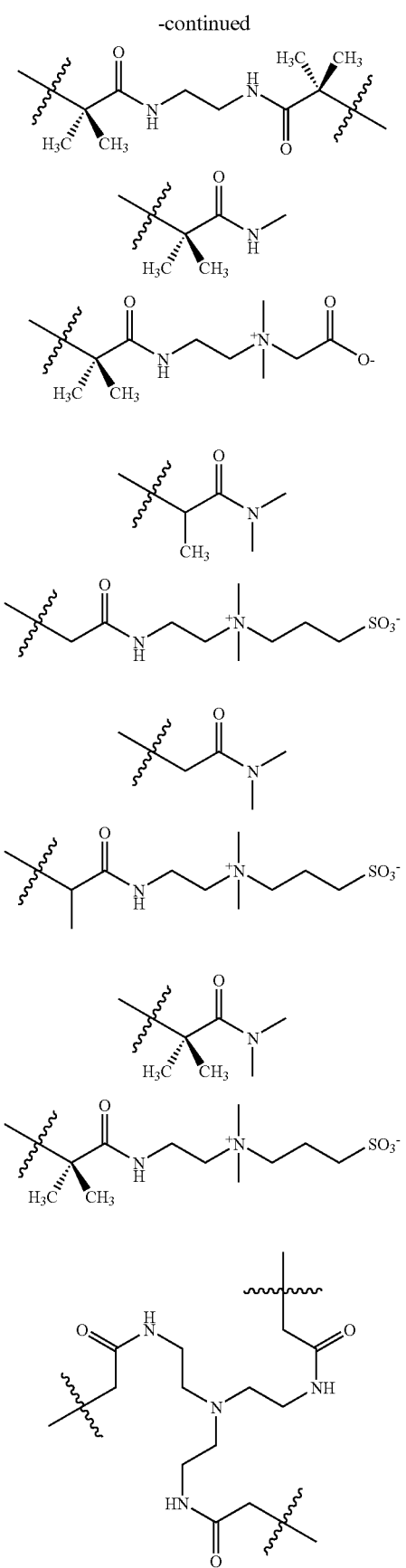

-continued
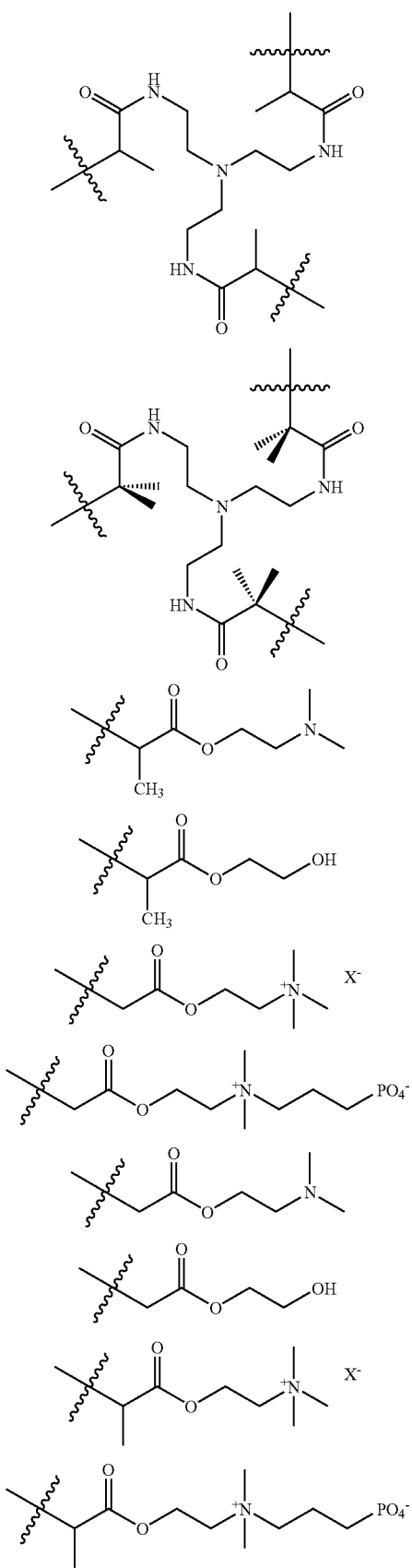
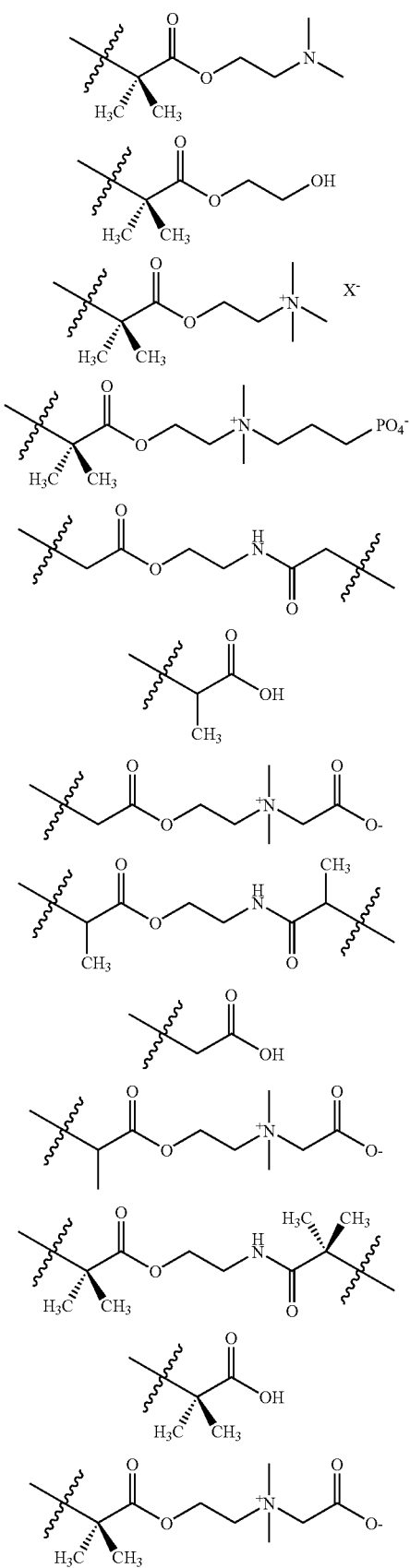

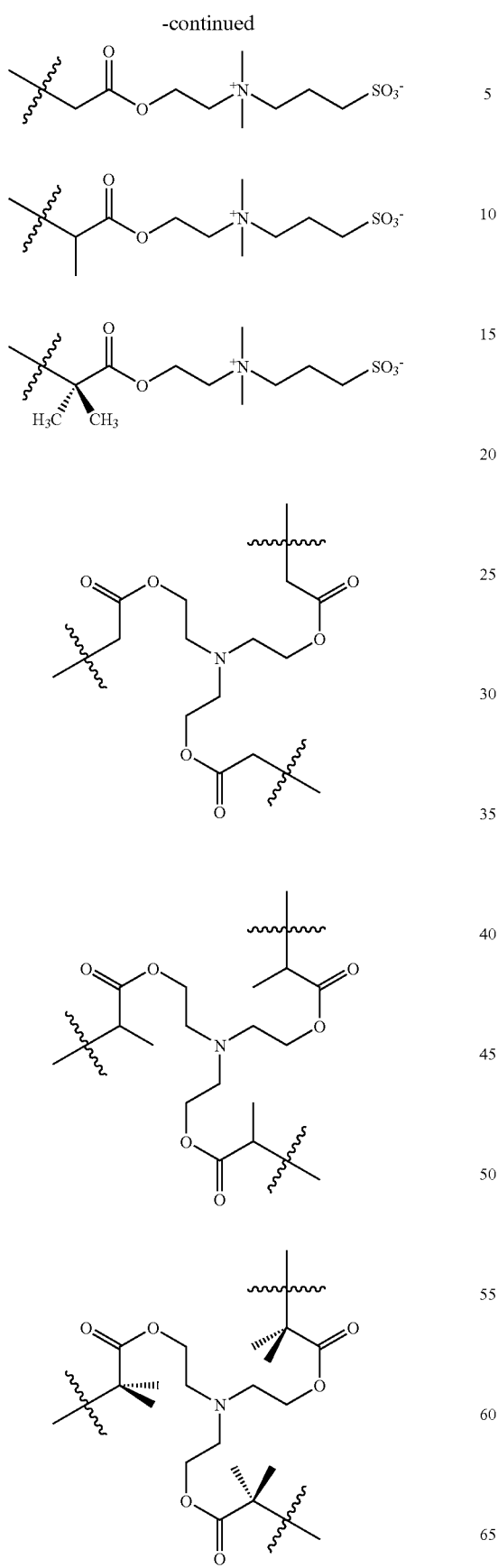
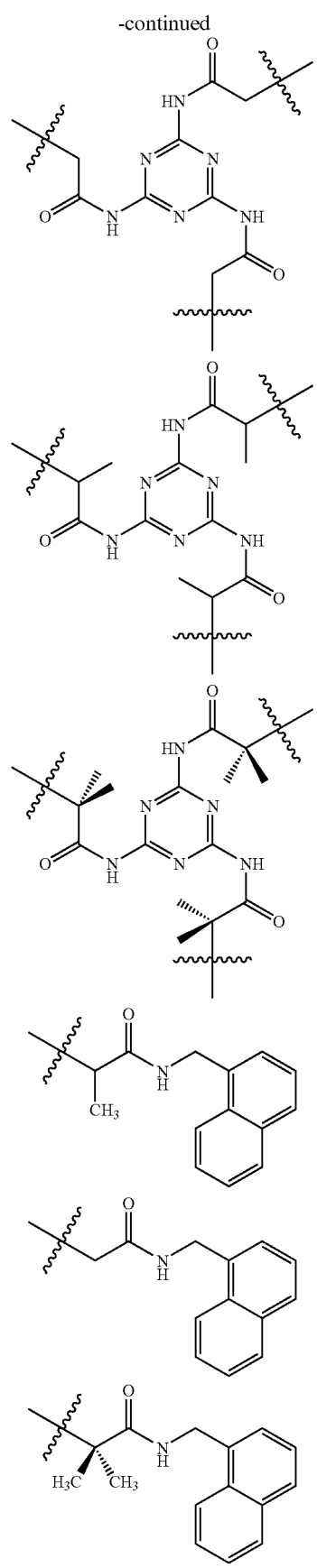

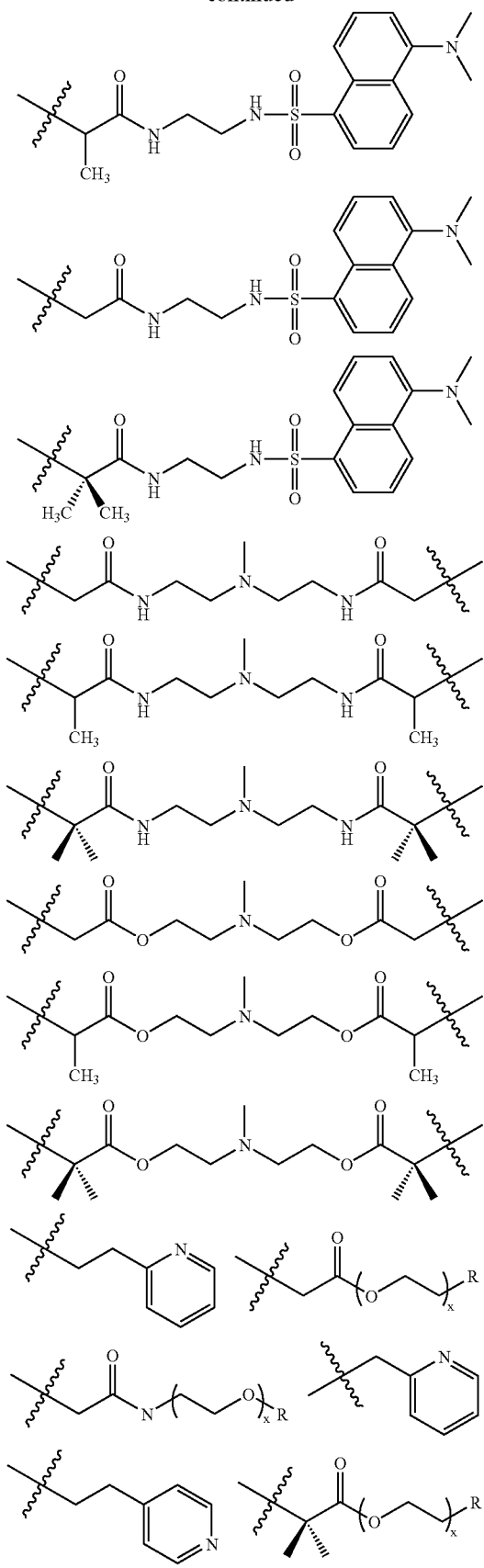
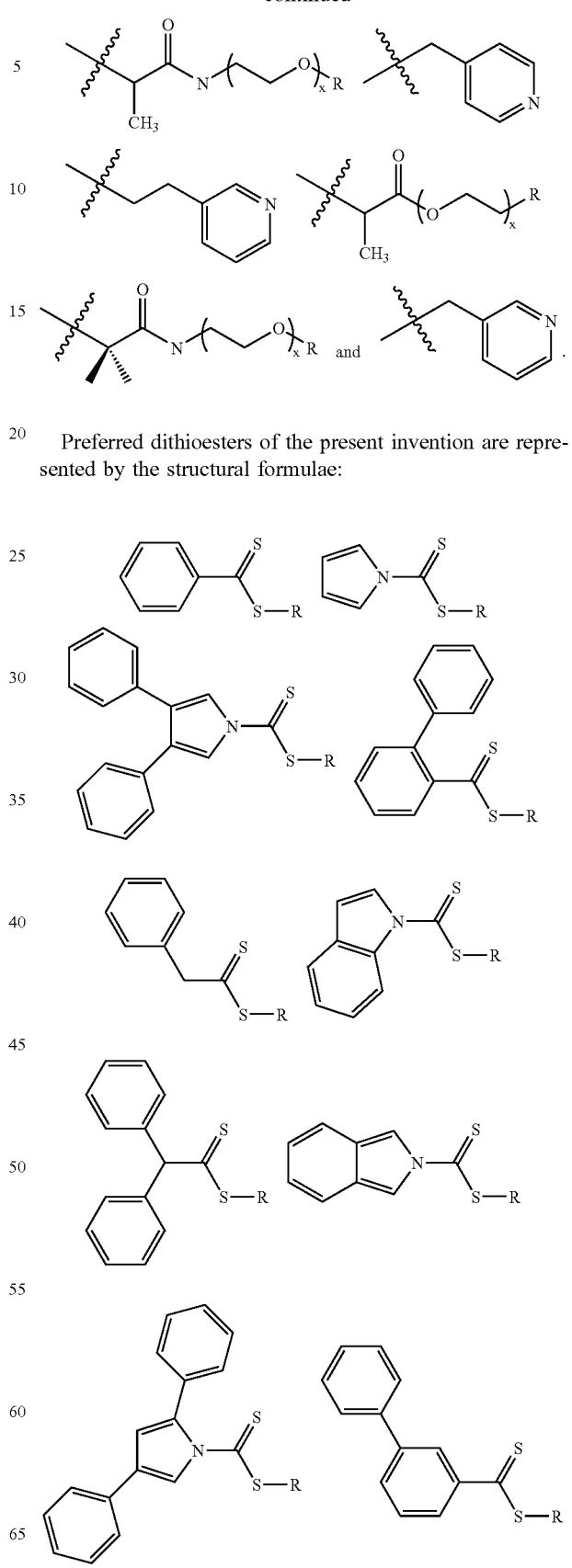
Preferred dithioesters of the present invention are represented by the structural formulae:

-continued
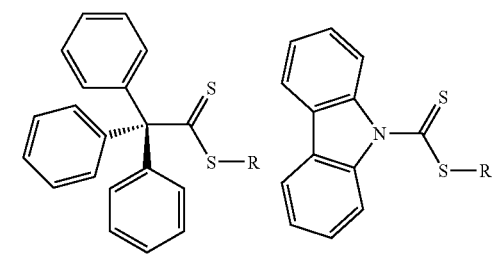
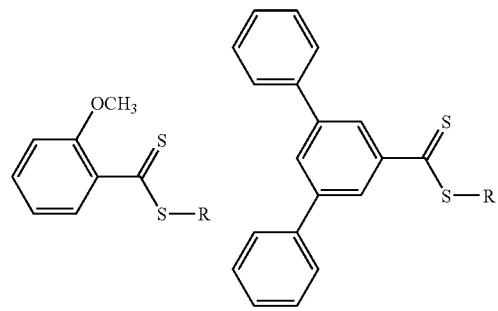
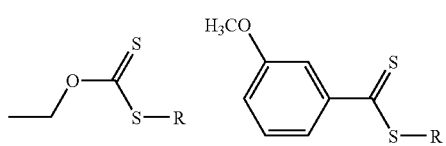
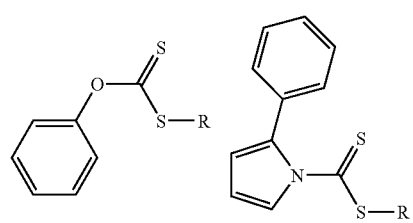
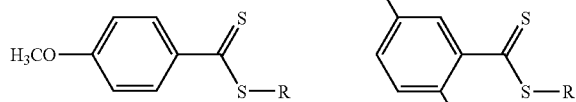
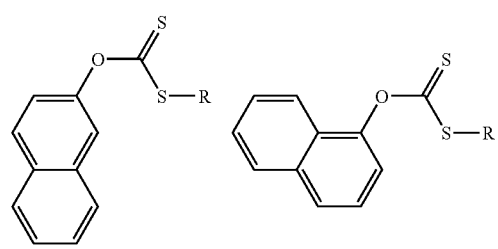
-continued
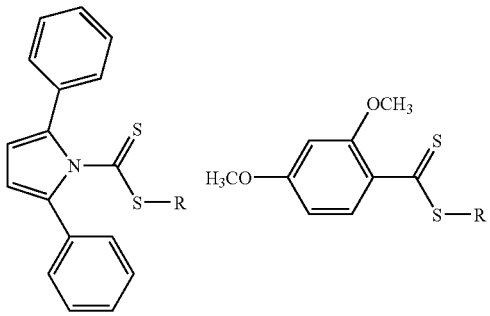
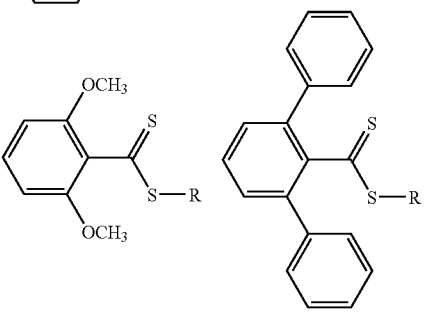
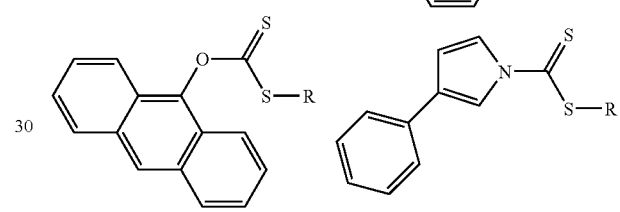
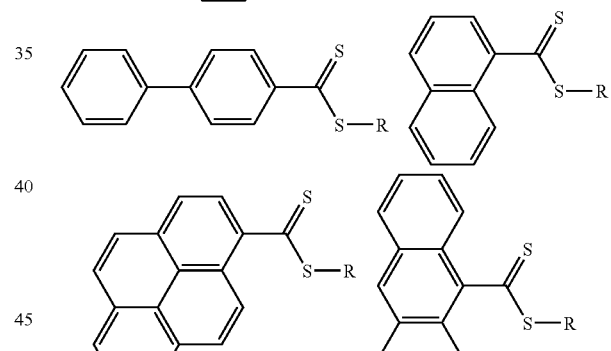
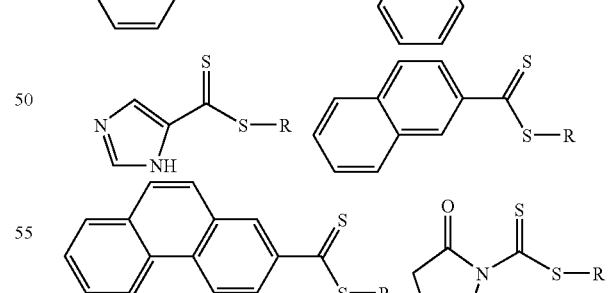
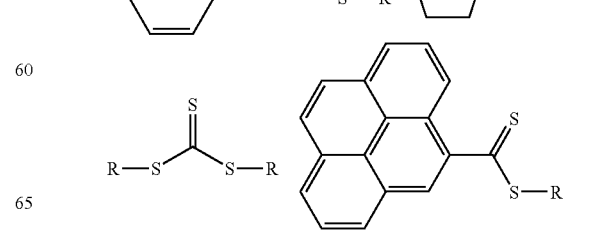

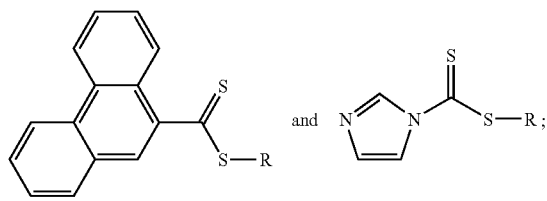

where R is as previously defined.

Especially preferred dithioesters of the present invention are represented by the structural formulae:

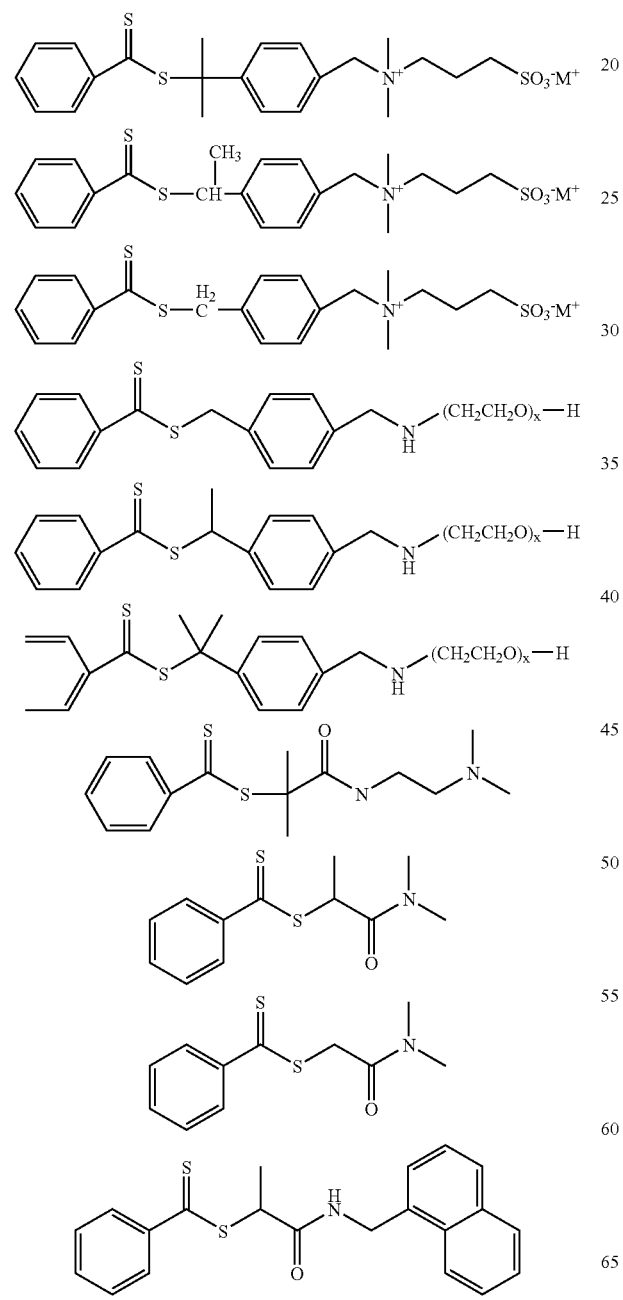

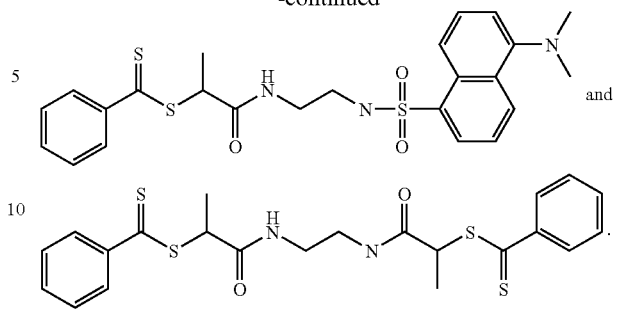

In another preferred embodiment, the dithioester is represented by the structural formula:

where:
- j is an integer from 1 to about 12, preferably 1 to about 6, more preferably 1 to 4, and even more about preferably 2;
- k is an integer from 0 to 5, preferably 0 or 1, more preferably 0;
- each $R_p$ is the same or different and is selected from the group consisting of —$SO_3^-M^+$, —COOH, —$COO^-M^+$, —$NH_2$, —$NR'_2$, —NR'H, —$NR'_3{}^+X^-$, $PO_4^-M^+$, —OH, —$(OCH_2CH_2)_xOH$, —$CONH_2$, —CONHR', —$CONR'_2$, —$NR'(CH_2)_xCOO^-M^+$, —$NR'(CH_2)_xOPO_3^-M^+$, —$NR'(CH_2)_xSO_3^-M^+$, —$N^+R'_2(CH_2)_xCOO^-M^+$, —$N^+R'_2(CH_2)_xOPO_3^-M^+$, —$N^+R'_2(CH_2)_xSO_3^-M^+$ and —SCN;
- W is selected from the group consisting of —$SO_3^-M^+$, —COOH, —$COO^-M^+$, —$PO_4^-M^+$, —$NR'_2$, —$NR'_3{}^+X^-$, —$NR'(CH_2)_xCOO^-M^+$, —$NR'(CH_2)_xOPO_3^-M^-$, —$NR'(CH_2)_xSO_3^-M^+$, —$N^+R'_2(CH_2)_xCOO^-M^+$, —$N^+R'_2(CH_2)_xOPO_3^-M^+$ and —$N^+R'_2(CH_2)_xSO_3^-M^+$; preferably —$SO_3^-M^+$;
- $M^+$ is ammonia, an ammonium ion, an alkali metal ion, an alkaline earth metal ion, or hydronium, preferably an alkali metal ion such as sodium;
- R' is independently hydrogen or an alkyl group
- $X^-$ is selected from the group consisting of halide, sulfate, phosphate, carboxylate and sulfonate; and
- x is an integer from 1 to about 20.

While not being bound by any one mechanism, RAFT polymerizations with a singly-functional chain transfer agent (CTA), such as a dithioester, are thought to occur by the mechanism illustrated in Scheme 1. Briefly, an initiator produces a free radical, which subsequently reacts with a polymerizable monomer. The monomer radical reacts with other monomers and propagates to form a chain, $P_n{}^\bullet$, which can react with a CTA. The CTA can fragment, either forming $R^\bullet$, which will react with another monomer that will form a new chain, $P_m{}^\bullet$, or $P_n{}^\bullet$, which will continue to propagate. In theory, propagation of $P_m{}^\bullet$ and $P_n{}^\bullet$ will continue until no monomer is left and a termination step occurs. After the first polymerization has finished, in particular circumstances, a second monomer can be added to the system to form a block copolymer. The present invention can also be used to synthesize multiblock, graft, star, gradient, and end-functional polymers.

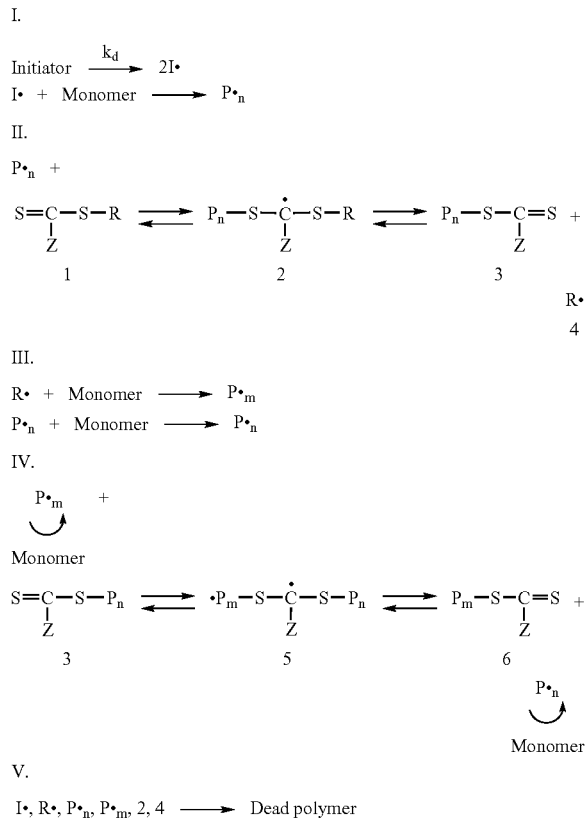

Scheme 1

Suitable polymerizable monomers and comonomers of the present invention include methyl methacrylate, ethyl acrylate, propyl methacrylate (all isomers), butyl methacrylate (all isomers), 2-ethylhexyl methacrylate, isobornyl methacrylate, methacrylic acid, benzyl methacrylate, phenyl methacrylate, methacrylonitrile, alpha-methylstyrene, methyl acrylate, ethyl acrylate, propyl acrylate (all isomers), butyl acrylate (all isomers), 2-ethylhexyl acrylate, isobornyl acrylate, acrylic acid, benzyl acrylate, phenyl acrylate, acrylonitrile, styrene, acrylates and styrenes selected from glycidyl methacrylate, 2-hydroxyethyl methacrylate, hydroxypropyl methacrylate (all isomers), hydroxybutyl methacrylate (all isomers), N,N-dimethylaminoethyl methacrylate, N,N-diethylaminoethyl methacrylate, triethyleneglycol methacrylate, itaconic anhydride, itaconic acid, glycidyl acrylate, 2-hydroxyethyl acrylate, hydroxypropyl acrylate (all isomers), hydroxybutyl acrylate (all isomers), N,N-dimethylaminoethyl acrylate, N,N-diethylaminoethyl acrylate, triethyleneglycol acrylate, methacrylamide, N-methylacrylamide, N,N-dimethylacrylamide, N-tert-butylmethacrylamide, N-n-butylmethacrylamide, N-methylolacrylamide, N-ethylolacrylamide, vinyl benzoic acid (all isomers), diethylaminostyrene (all isomers), alpha-methylvinyl benzoic acid (all isomers), diethylamino alpha-methylstyrene (all isomers), p-vinylbenzenesulfonic acid, p-vinylbenzene sulfonic sodium salt, trimethoxysilylpropyl methacrylate, triethoxysilylpropyl methacrylate, tributoxysilylpropyl methacrylate, dimethoxymethylsilylpropyl methacrylate, diethoxymethylsilylpropylmethacrylate, dibutoxymethylsilylpropyl methacrylate, diisopropoxymethylsilylpropyl methacrylate, dimethoxysilylpropyl methacrylate, diethoxysilylpropyl methacrylate, dibutoxysilylpropyl methacrylate, diisopropoxysilpropyl methacrylate, trimethoxysilylpropyl acrylate, triethoxysilylpropyl acrylate, tributoxysilylpropyl acrylate, dimethoxymethylsilylpropyl acrylate, diethoxymethylsilylpropyl acrylate, dibutoxymethylsilylpropyl acrylate, diisopropoxymethylsilylpropyl acrylate, dimethoxysilylpropyl acrylate, diethoxysilylpropyl acrylate, dibutoxysilylpropyl acrylate, diisopropoxysilylpropyl acrylate, vinyl acetate, vinyl butyrate, vinyl benzoate, vinyl chloride, vinyl fluoride, vinyl bromide, maleic anhydride, N-phenylmaleimide, N-butylmaleimide, N-vinylpyrrolidone, N-vinylcarbazole, butadiene, isoprene, chloroprene, ethylene, propylene, 1,5-hexadienes, 1,4-hexadienes, 1,3-butadienes, and 1,4-pentadienes.

Additional suitable polymerizable monomers and comonomers include vinylalcohol, vinylamine, N-alkylvinylamine, allylamine, N-alkylallylamine, diallylamine, N-alkyldiallylamine, alkylenimine, acrylic acids, alkylacrylates, acrylamides, methacrylic acids, alkylmethacrylates, methacrylamides, N-alkylacrylamides, N-alkylmethacrylamides, styrene, vinylnaphthalene, vinyl pyridine, ethylvinylbenzene, aminostyrene, vinylbiphenyl, vinylanisole, vinylimidazolyl, vinylpyridinyl, dimethylaminomethylstyrene, trimethylammonium ethyl methacrylate, trimethylammonium ethyl acrylate, dimethylamino propylacrylamide, trimethylammonium ethylacrylate, trimethylammonium ethyl methacrylate, trimethylammonium propyl acrylamide, dodecyl acrylate, octadecyl acrylate, and octadecyl methacrylate.

Preferred polymerizable monomers and comonomers include alkylacrylamides, methacrylamides, acrylamides, styrenes, allylamines, allylammonium, diallylamines, diallylammoniums, alkylacrylates, methacrylates, acrylates, n-vinyl formamide, vinyl ethers, vinyl sulfonate, acrylic acid, sulfobetaines, carboxybetaines, phosphobetaines, and maleic anhydride.

Even more preferred polymerizable monomers and comonomers include alkylacrylates, methacrylates, acrylates, alkylacrylamides, methacrylamides, acrylamides, and styrenes.

Especially preferred monomers and comonomers include acrylamide, 2-acrylamido-2-methylpropane sulfonate, 3-acrylamido-3-methylbutanoate, N,N-dimethylacrylamide, vinyl benzoic acid, vinyl N,N,N-trimethylammoniomethylbenzene, vinyl N,N-dimethylaminomethylbenzene and styrene sulfonate.

The source of free radicals can be any suitable method of generating free radicals such as thermally induced homolytic scission of a suitable compound(s) (thermal initiators such as peroxides, peroxyesters, or azo compounds), the spontaneous generation from a monomer (e.g., styrene), redox initiating systems, photochemical initiating systems or high energy radiation such as electron beam, X- or gamma-ray radiation. The initiating system is chosen such that under the reaction conditions, there is no substantial adverse interaction of the initiator, the initiating conditions, or the initiating radicals with the transfer agent under the conditions of the procedure. The initiator should also have the requisite solubility in the reaction medium or monomer mixture.

Thermal initiators are chosen to have an appropriate half-life at the temperature of polymerization. These initiators can include one or more of 2,2'-azobis(isobutyronitrile), 2,2'-azobis(2-cyano-2-butane), dimethyl 2,2'-azobisdimethylisobutyrate, 4,4'-azobis(4-cyanopentanoic acid), 1,1'-azobis(cyclohexanecabonitrile), 2-(t-butylazo)-2-cyanopropane, 2,2-azobis[2-methyl-N-(1,1)-bis(hydroxyethyl)]-propionamide, 2,2'-azobis(N,N'-dimethyleneisobutyramidine) dihydrochloride, 2,2'-azobis (N,N'-dimethyleneisobutyramine), 2,2'-azobis(2-methyl-N-[1,1-bis(hydroxymethyl)-2-hydroxyethyl] propionamide, 2,2'-azobis[2-methyl-N-(2-hydroxyethyl)propionamide], 2,2'-azobis(isobutyramide) dihydrate, 2,2'-azobis(2,2,4-trimethylpentane), 2,2'-azobis (2-methylpropane), t-butyl peroxyacetate, t-butyl peroxybenzoate, t-butyl peroxyoctoate, t-butyl peroxyneodecanoate, t-butylperoxy isobutyrate, t-amyl peroxypivalate, t-butyl peroxypivalate, di-isopropyl peroxydicarbonate, dicyclohexyl peroxydicarbonate, dicumyl peroxide, dibenzoyl peroxide, dilauroyl peroxide, potassium peroxydisulfate, ammonium peroxydisulfate, di-t-butyl, hyponitrite, and dicumyl hyponitrite.

Photochemical initiator systems are chosen to have the requisite solubility in the reaction medium or monomer mixture and have an appropriate quantum yield for radical production under the conditions of the polymerization. Examples include benzoin derivatives, benzophenone, acyl phosphine oxides, and photo-redox systems.

Redox initiator systems are chosen to have the requisite solubility in the reaction medium or monomer mixture and have an appropriate rate of radical production under the conditions of the polymerization; these initiating systems can include combinations of oxidants such as potassium peroxydisulfate, hydrogen peroxide, t-butyl hydroperoxide and reductants such as iron(II), titanium(III), potassium thiosulfite, and potassium bisulfite.

Other suitable initiating systems are described in recent texts. See, for example, Moad and Solomon, "The Chemistry of Free Radical Polymerization," Pergamon, London, 1995, pp. 53–95.

Polymerizations of the present invention can occur in any suitable solvent or mixture thereof. Suitable solvents include water, alcohol (e.g., methanol, ethanol, n-propanol, isopropanol, butanol), tetrahydrofuran (THF) dimethyl sulfoxide (DMSO), dimethylformamide (DMF), acetone, acetonitrile, hexamethylphosphoramide, acetic acid, formic acid, hexane, cyclohexane, benzene, toluene, methylene chloride, ether (e.g., diethyl ether), chloroform, and ethyl acetate. Preferred solvents include water, and mixtures of water and water-miscible organic solvents such as DMF. Water is an especially preferred solvent.

In a preferred embodiment of the present invention, a polymer or copolymer is prepared where the following are reacted together in a solvent or solvent mixture (e.g., water or a mixture of water and dimethylformamide): N,N-dimethylacrylamide, N,N-dimethyl-s-thiobenzoylthio-2-propionamide or sodium thiobenzoylthio-s-4-cyano-4-pentanoate, and free radicals produced by a free radical source.

It desirable to choose reaction components (solvent, etc.), such that the components have a low transfer constant towards the propagating radical. Chain transfer to these species will lead to the formation of chains that do not contain an active dithioester group.

In addition to the choice of dithioester, monomer or comonomer, free radical source, and solvent, the choice of polymerization conditions is also important. The reaction temperature will influence the rate. For example, higher reaction temperatures will typically increase the rate of fragmentation. Conditions should be chosen such that the number of chains formed from initiator-derived radicals is minimized to an extent consistent with obtaining an acceptable rate of polymerization. Termination of polymerization by radical-radical reactions will lead to chains that contain no active group and therefore cannot be reactivated. The rate of radical-radical termination is proportional to the square of the radical concentration. Furthermore, in the synthesis of block, star, or branched polymers, chains formed from initiator-derived radicals will constitute a linear homopolymer impurity in the final product. The reaction conditions for these polymers therefore require careful choice of initiator concentration and, where appropriate, the rate of initiator feed.

As a general guide in choosing conditions for the synthesis of narrow dispersity polymers, the concentration of initiator(s) and other reaction conditions (solvent(s), temperature, pressure) should be chosen such that the molecular weight of polymer formed in the absence of the CTA is at least twice that formed in its presence. In polymerizations where termination is solely by disproportionation, this equates to choosing an initiator concentration such that the total moles of initiating radicals formed during the polymerization is less than 0.5 times that of the total moles of CTA. More preferably, conditions should be chosen such that the molecular weight of polymer formed in the absence of the CTA is at least 5-fold that formed in its presence.

The polydispersity of polymers and copolymers synthesized by the method of the present invention can be controlled by varying the ratio of the numbers of molecules of CTA to initiator. A lower polydispersity is obtained when the ratio of CTA to initiator is increased. Conversely, a higher polydispersity is obtained when the ratio of CTA to initiator is decreased. Preferably, conditions are selected such that polymers and copolymers have a polydispersity less than about 1.5, more preferably less than about 1.3, even more preferably less than about 1.2, and yet more preferably less than about 1.1. In conventional free radical polymerizations, polydispersities of the polymers formed are typically in the range of 1.6–2.0 for low conversions (<10%) and are substantially greater than this for higher conversions. For the polymerization of monomers or comonomers based on acrylamide (e.g., having an acrylamide moiety), acceptable polydispersities have been obtained when the ratio of CTA (e.g., a dithioester or trithioester of the present invention) to initiator (free radical source) is about 0.8 to about 1.6, about preferably 0.9 to about 1.5, more preferably about 1.0 to about 1.4 or still more preferably about 1.1 to about 1.3.

With these provisos, the polymerization process according to the present invention is performed under the conditions typical of conventional free-radical polymerization. Polymerizations employing the above described dithioesters are suitably carried out at temperatures in the range −20 to 200° C., preferably 20 to 150° C., more preferably 50 to 120° C., or even more preferably 60 to 90° C. The pH of a polymerization conducted in aqueous solution can also be varied. The pH is selected in part so that the selected dithioester is stable and propagation of the polymer occurs. Typically, the pH is from about 0 to about 9, preferably from about 1 to about 7, more preferably from about 2 to about 6.5. The pH can be adjusted following polymerization, particularly when the polymer is a copolymer, such that one monomer of the copolymer is charged and another monomer is uncharged or of opposite charge.

As discussed above, when the monomer or comonomer is acrylamide or contains an acrylamide moiety, the polymerization is advantageously carried out in an acidic solution, such as a buffered aqueous solution. An acetate buffer, for example, has been found to work well. The pH of such solutions typically is greater than about 1 and less than about 7, more typically greater than about 2 and less than about 7, still more typically greater than about 4 and less than about 6 or, in certain instances, greater than about 4.5 and less than about 5.5.

Aromatic groups of the dithioesters, as defined herein, include carbocyclic aromatic groups such as phenyl, benzyl, 1-naphthyl, 2-naphthyl, 1-anthracyl, 2-anthacyl, phenanthrenyl, pyrenyl, and biphenyl. Heterocyclic aromatic groups include groups such as N-imidazolyl, 2-imidazole, 1-pyrrolyl, 2-pyrrolyl, 3-pyrrolyl, 2-thienyl, 3-thienyl, 2-furanyl, 3-furanyl, 2-pyridyl, 3-pyridyl, 4-pyridyl, 2-pyrimidyl, 4-pyrimidyl, 2-pyranyl, 3-pyranyl, 3-pyrazolyl, 4-pyrazolyl, 5-pyrazolyl, 2-pyrazinyl, 2-thiazole, 4-thiazole, 5-thiazole, 2-oxazolyl, 4-oxazolyl and 5-oxazolyl.

Heteroaromatic groups also include fused polycyclic aromatic ring systems in which a carbocyclic aromatic ring or heteroaryl ring is fused to one or more other heteroaryl rings. Examples include 2-benzothienyl, 3-benzothienyl, 2-benzofuranyl, 3-benzofuranyl, 1-indolyl, 2-indolyl, 3-indolyl, 2-quinolinyl, 3-quinolinyl, 2-benzothiazole, 2-benzooxazole, 2-benzimidazole, 2-quinolinyl, 3-quinolinyl, 1-isoquinolinyl, 3-quinolinyl, 1-isoindolyl, 3-isoindolyl, and carbazoyl.

An alkyl group of the present dithioesters is a saturated hydrocarbon in a molecule that is bonded to one other group in the molecule through a single covalent bond from one of its carbon atoms. Examples of alkyl groups include methyl, ethyl, n-propyl, iso-propyl, n-butyl, sec-butyl and tert-butyl. An alkoxy group is an alkyl group where an oxygen atom connects the alkyl group and one other group (e.g., the alkyl group and the dithioester carbon). An alkylene group is a saturated hydrocarbon in a molecule that is bonded to two other groups in the molecule through single covalent bonds from two of its carbon atoms. Examples of alkylene groups include methylene, ethylene, propylene, iso-propylene (—CH(CH$_2$)CH$_2$—), butylene, sec-butylene (—CH(CH$_3$)CH$_2$CH$_2$—), and tert-butylene (—C(CH$_3$)$_2$CH$_2$—). An azaalkylene group is a saturated hydrocarbon comprising one or more nitrogen atoms in the chain in a molecule that is bonded to two other groups in the molecule through single covalent bonds from two of its carbon atoms.

Alkyl, oxyalkyl, alkylene, azaalkylene, aromatic and heteroaromatic groups can be substituted with functional groups including, for example, halogen (—Br, —Cl, —I and —F) —OR", —CN, —NO$_2$, —NH$_2$, —NHR", —NR"$_2$, —COOR", —CONR"$_2$, and —SO$_k$R" (k is 0, 1 or 2). Each R" is independently —H, an alkyl group, a substituted alkyl group, a benzyl group, a substituted benzyl group, an aromatic group or a substituted aromatic group. A substituted aromatic or heteroaromatic group can also have an alkyl or substituted alkyl group as a substituent. A substituted alkyl group can also have an aromatic or substituted aromatic group as a substituent. A substituted alkyl, oxyalkyl, alkylene, azaalkylene, aromatic or heteroaromatic group can have more than one substituent. A substituent should not appreciably interfere with a polymerization. For instance, a primary or secondary amine can react with and inactive a dithioester. Other acceptable functional groups include epoxy, hydroxy, alkoxy, acyl, acyloxy, carboxy, sulfonate, alkylcarbonyloxy, isocyanato, cyano, silyl, halo, and dialkylamino, each of which can undergo further chemical transformation, such as being joined with another polymer chain.

Alkali metal ions include lithium, sodium, and potassium ions. Alkaline earth metal ions include magnesium and calcium ions. Halides include fluoride, chloride, bromide, and iodide.

EXEMPLIFICATION

Example 1

Preparation of Poly(2-acrylamido-2-methylpropanesulfonate [AMPS]) and Poly(3-acrylamido-3-methylbutanoate [AMBA])

Anionic AMPS and AMBA homopolymers were synthesized in water by RAFT. 4,4'-azobis(4-cyanopentanoic acid) was the initiator and 4-cyanopentanoic acid dithiobenzoate was the RAFT chain transfer agent (CTA). The reactions were carried out at 70° C. under a nitrogen atmosphere, in round-bottomed flasks, equipped with a magnetic stir bar and sealed with a rubber septum. The initiator: CTA ratio was 5:1 on a molar basis. The monomer concentration was 2.0 M. The solution pH was adjusted to ~9.6±0.2 (such that AMBA was fully ionized). Aliquots (0.74 mL) were removed from the polymerizations, via syringe, approximately every hour, diluted 100 fold with eluent and then characterized by aqueous size exclusion chromatography (ASEC) (20% MeCN/80% 0.1 M NaNO$_3$ eluent, Viscotek TSK Viscogel column, Spectraphysics UV2000 detector, HP 1047A RI detector, poly(sodium 4-styrensulfonate) standards). The results for the synthesis of the AMPS and AMBA homopolymers are summarized in Table 1.

TABLE 1

| Sample | Time (min) | Conversion (%) | $M_n$ (theory) | $M_n$ (expt)[a] | $M_w$ (expt)[a] | $M_w/M_n$[a] |
|---|---|---|---|---|---|---|
| AMPS1 | 255 | 77.1 | 26,500 | 24,400 | 31,500 | 1.29 |
| AMPS2 | 343 | 88.0 | 17,600 | 19,500 | 22,600 | 1.16 |
| AMPS3 | 8 | >95.0[a] | — | — | — | — |
| AMBA1 | 255 | 65.5 | 21,800 | 14,000 | 18,200 | 1.30 |
| AMBA2 | 346 | 74.8 | 15,000 | 12,100 | 14,800 | 1.22 |
| AMBA3 | 8 | >95.0[a] | — | — | — | — |
| PAMPS macro-CTA | — | — | — | 33,900 | 38,600 | 1.14 |
| P(AMPS-b-AMBA) | — | — | 68,500 | 69,700 | 79,500 | 1.14 |
| PAMBA macro-CTA | — | — | — | 31,300 | 35,300 | 1.14 |
| P(AMBA-b-AMPS) | — | — | 64,400 | 57,900 | 67,200 | 1.16 |

[a]As determined by aqueous size exclusion chromatography, calibrated with poly(sodium 4-styrenesulfonate) standards in 20% MeCN/80% 0.1 M NaNO$_3$ eluent.

The CTA: monomer ratios were such that the theoretical $M_n$, at 100% conversion, for AMPS1 was 34,400 g/mol and 20,000 g/mol for AMPS2. A single AMPS homopolymer (AMPS3) was also synthesized by conventional free radical polymerization as a control. The experimental details were the same as the RAFT polymerizations except CTA was not added. In this instance, the reaction solution gelled within ~10 min. AMBA homopolymers were synthesized under identical conditions as the AMPS homopolymers and similar results were obtained.

AMPS and AMBA homopolymers were subsequently employed as macro-CTAs for the block copolymerization of the opposite monomer (i.e. RAFT mediated Poly(AMPS) was used as the macro-CTA for the RAFT polymerization of AMBA, yielding a diblock copolymer of poly(AMPS-block-AMBA), and vice-versa). Due to the high viscosities of the aqueous solutions of monomer and macro-CTA, the monomer concentration was reduced to 1.0 M for the block copolymerizations as opposed to the 2.0 M concentrations used in the preparation of the homopolymers. Given the lower monomer concentration polymerization times were extended to approximately 13 h as compared to 6.5 h for the homopolymerizations. Proton NMR was conducted and the peaks were assigned for the homopolymers of AMPS and AMBA, as well as the corresponding poly(AMPS-block-AMBA) copolymer.

The copolymer was seen to be composed of monomeric units derived from both AMPS and AMBA. Integration of the peaks associated with the methylene protons adjacent to the anionic functionalities yielded a copolymer composition of 46:54 (mol % basis) (AMPS:AMBA). This was in excellent agreement with the theoretical target composition of 45:55. Likewise the block copolymer composition for the AMBA-AMPS diblock was found to be 49:51, with a target theoretical composition of 47:53.

Also listed in Table 1 is a summary of the molecular weights and polydispersities for the macro-CTAs and the corresponding block copolymers. Molecular weight distributions were determined using a Viscotek TRISEC detector, calibrated with poly(4-sodium styrenesulfonate) standards in the eluent described above. Data analysis was performed using software written in-house.

Example 2

Synthesis of N,N-dimethyl-s-thiobenzoylthiopropionamide

The title compound was synthesized in a manner similar to that reported by Bhandari, C. S.; Mahnot, U. S.; Sognani, N. C. *Journal Für Praktische Chemie* 1971, 313, 849. To a 100 mL round-bottomed flask was added 2-mercaptopropionic acid (50.0 mL, 0.56 mol). Dimethylamine (23.9 g, 0.53 mol) was added to the solution while keeping the reaction flask in a water bath. Excess dimethylamine was removed using a water aspirator. The reaction was heated at 110° C. for an extended period, during which time the reaction took on a light yellow color. The product was fractionally distilled under reduced pressure. The major crude fraction, which was collected at approximately 80° C. (0.02 mmHg), was determined to contain 57% of the target compound and 43% acid precursor. The acid impurity was removed by washing with dilute $NaOH/CH_2Cl_2$. The $CH_2Cl_2$ was removed using a rotary evaporator and the target compound purified by vacuum distillation (bp 80° C. at 0.02 mmHg). Yield=45%. $^1$H NMR (CDCl$_3$) δ (ppm) 1.53 (d, —CH$_3$), 2.11 (s, —SH), 2.99 (s —CONCH$_3$), 3.16 (s-CONCH$_3$), 3.67 (m-CH).

Carboxymethyl dithiobenzoate (5.00 g, 23.60 mmol) was mixed with deionized water (20 ml) and neutralized with a dilute solution of sodium carbonate to a final volume of 130 ml. Subsequently, N,N-dimethyl-2-mercaptopropionamide (3.13 g, 15.0 mmol) was added to the sodium carboxymethyl dithiobenzoate solution. After 24 hours the contents of the flask were poured into a separatory funnel and a dark red oil isolated. The aqueous phase was washed with diethyl ether (30.0 mL) to extract the remaining product. Subsequently, the products were dissolved in diethyl ether (50.0 mL) and washed with deionized H$_2$O (25.0 mL). The diethyl ether phase was separated and dried over anhydrous sodium sulfate. The solution was filtered and the solvent removed via a rotary evaporator. The product was isolated as deep orange plates by recrystallization from a mixture of methanol/water (3:2 v/v). Yield=52%. Melting point=61–62° C. $^1$H NMR (d$_6$-DMSO) δ (ppm): 1.52 (d, —CH$_3$) 2.88 (s, —N—CH$_3$), 3.08 (s, —N—CH$_3$), 5.04 (m —CH), 7.50, 7.66, 7.96 (m, —CH). $^{13}$C NMR (d$_6$-DMSO) δ (ppm): 16.54 (CH$_3$), 35.46 (N—CH$_3$), 36.86 (N—CH$_3$), 47.15 (CH), 126.42, 128.70. 133.04, 143.71 (CH), 169.02 (C═O), 226.46 (CS$_2$). IR (KBr Disc): 1643.1 (C═O); 1039.9 (C═S). CHNS elemental microanalysis for C$_{12}$H$_{15}$NOS$_2$— Calculated: C, 56.88%; H, 5.97%; N, 5.53%; S, 25.31%. Found C, 56.89%; H, 5.74%; N, 5.48%; S, 25.19%.

In FIG. 1 are shown the SEC chromatograms (RI response) for aliquots of the polymerization at various time intervals (FIG. 1a), along with the kinetic plot (FIG. 1b) and the molecular weight vs. conversion and polydispersity vs. conversion plots (FIG. 1c).

The SEC chromatograms in FIG. 1a clearly show the increase in molecular weight with time. Also noted is the appearance of a higher molecular weight species—evidenced as shoulder, at extended polymerization time. The kinetic plot in FIG. 1b show 1$^{st}$ order behavior, implying a constant number of radicals. The number average molecular weight increased in a linear fashion with conversion (FIG. 1c), at least up to approximately 60%, and is characteristic of a controlled or living process. The polydispersity showed an initial decrease with increasing conversion and then began to increase slightly. At all times the polydispersity remained low ($M_w/M_n$<1.25)—well below the theoretical lowest limit of 1.50 for a conventional free radical polymerization.

Example 3

Synthesis of N,N-dimethyl-s-thiobenzoylthioacetamide

N,N-Dimethyl-2-mercaptoacetamide was synthesized in a similar fashion to N,N-dimethyl-2-mercaptopropionamide. 2-Thioglycolic acid (50.0 ml, 0.563 mol) was reacted with dimethylamine (23.9 g, 0.53 mol) in the manner reported above. The reaction was allowed to proceed at 110° C. for 5 days. The product was then distilled and purified. The product was purified via vacuum distillation (bp 112° C. at 1.0 mmHg). Yield=68%. $^1$H NMR (CDCl$_3$) δ (ppm) 2.41 (s, —SH), 2.99 (s —CONCH$_3$), 3.08 (s —CONCH$_3$), 3.36 (m-CH$_2$).

Carboxymethyl dithiobenzoate (30.22 g, 142.0 mmol) was neutralized with a dilute aqueous solution of sodium carbonate. N,N-dimethyl-2-mercaptoacetamide (16.28 g, 15.0 mmol) was subsequently added to the sodium carboxymethyl dithiobenzoate solution. The reaction was allowed to proceed for 24 h. The product was subsequently extracted with diethyl ether and dried over anhydrous sodium sulfate. The solution was filtered and the solvent removed via a rotary evaporator. The product was isolated as deep orange needles by recrystallization from a mixture of methanol/water (3:2 v). Yield=57%. Melting point 63–64° C. $^1$H NMR (d$_6$-DMSO) δ (ppm): 2.88 (s, —N—CH$_3$), 3.12 (s, —N—CH$_3$), 4.48 (s —CH$_2$), 7.50, 7.66, 7.98 (m,—CH). $^{13}$C NMR (d$_6$-DMSO) δ (ppm): 35.29 (N—CH$_3$), 36.98 (N—CH$_3$), 41.008 (CH$_2$), 126.35, 128.66, 132.88, 144.23 (CH), 165.20 (C═O), 227.29 (CS$_2$). IR (KBr Disc): 1654.6 (C═O); 1045.3 (C═S). CHNS elemental microanalysis for C$_{11}$H$_{13}$NOS$_2$—Calculated: C, 55.20%; H, 5.47%, N, 5.85%, S, 26.79%. Found C, 55.11%; H, 5.37%; N, 5.84%; S, 26.86%.

Example 4

RAFT Polymerization of N,N-Dimethylacrylamide

Polymerizations of N,N-dimethylacrylainide (DMA) in benzene were conducted at 60° C. in flame sealed ampoules equipped with magnetic stir bars, whereas polymerizations in d$_6$-benzene were performed in flame sealed NMR tubes. All polymerizations were performed at monomer concentrations of ~1.93 M in benzene, with AIBN as the free radical initiator. The chain transfer agent was N,N-dimethyl-s-thiobenzoylthiopropionamide or N,N-dimethyl-s-thiobenzoyl-thioacetamide. Polymerizations at a CTA/I ratio of 5/1, in $d_6$-benzene, were performed at an initiator concentration of $9.52 \times 10^4$ mol, for a target molecular weight of 40,000. Similarly, the polymerizations conducted at a CTA/I ratio of 80/1, in benzene, were performed at an initiator concentration of $6.28 \times 10^{-5}$ mol, for a target molecular weight of 40,000. The ampoules were subjected to three freeze-pump-thaw cycles to remove oxygen from the DMA solutions and were subsequently placed in a pre-heated water-bath or inserted into the DMR spectrometer with the temperature maintained at 60° C. Termination of the polymerizations was achieved by freezing the reactions in a dry ice/acetone bath. The polymers were isolated by precipitation into hexane, filtered, redissolved in THF and re-precipitated into hexane. Conversions were determined gravimetrically (polymerizations at a CTA/I ratio of 80/1) or by $^1$H NMR spectroscopy (polymerizations at a CTA/I ratio of 5/1).

Example 5

A comparative study of the RAFT Polymerization of DMA in the presence of CTAs (1a—benzyl dithiobenzoate (BDB), 1b—isopropyl cumyl dithiobenzoate (CDB), 1c—N,N-dimethyl-s-thiobenzoylthiopropionamide (TBP), 1d—N,N-dimethyl-s-thiobenzoylthioacetamide (TBA))

RAFT polymerizations of N,N-dimethylacrylamide (DMA) were conducted in benzene at 60° C. using AIBN as the initiator. Polymerizations were performed in degassed, flame sealed glass reactors in order to preclude any possible oxidation of the CTAs. Pertinent data including CTA/I ratios, reaction times, conversions, and molecular weights are given in Table 2.

TABLE 2

Data from the RAFT polymerization of DMA with CTAs 1a–1d (target MW = 40,000) in $d_6$-benzene (60° C.) using a CTA/I ratio of 5/1: [M] = 1.92, [CTA] = $4.81 \times 10^{-3}$, [I] = $9.52 \times 10^{-4}$.

| CTA | Time(h) | % Conversion | $Mn_{Th}$ | $Mn_{SEC}^B$ | $M_w/M_n$ |
|---|---|---|---|---|---|
| 1a | 14.5 | 80 | 32,000 | 50,700 | 1.22 |
| 1a | 36.6 | 90 | 36,000 | 51,200 | 1.22 |
| 1a | 66.5 | 97 | 38,800 | 53,200 | 1.24 |
| 1a | 156.0 | 98 | 39,200 | 55,300 | 1.27 |
| 1a | 181.5 | 98 | 39,200 | 59,700 | 1.23 |
| 1a | 186.2 | 98 | 39,200 | 60,000 | 1.24 |
| 1b | 8.1 | 59 | 23,600 | 35,800 | 1.12 |
| 1b | 36.6 | 86 | 34,400 | 45,800 | 1.25 |
| 1b | 66.5 | 95 | 38,000 | 54,600 | 1.24 |
| 1b | 156.0 | 96 | 38,400 | 53,100 | 1.24 |
| 1b | 181.5 | 96 | 38,400 | 53,400 | 1.25 |
| 1b | 186.2 | 96 | 38,400 | 55,700 | 1.26 |
| 1c | 19.0 | 78 | 31,200 | 35,200 | 1.14 |
| 1c | 36.6 | 82 | 32,800 | 42,600 | 1.14 |
| 1c | 66.5 | 93 | 37,200 | 48,500 | 1.19 |
| 1c | 156.0 | 94 | 37,600 | 49,100 | 1.15 |
| 1c | 186.2 | 95 | 37,992 | 53,400 | 1.18 |
| 1d | 10.9 | 67 | 26,800 | 39,400 | 1.15 |
| 1d | 36.6 | 82 | 32,800 | 47,900 | 1.20 |
| 1d | 66.5 | 96 | 38,400 | 49,600 | 1.24 |
| 1d | 156.0 | 97 | 38,800 | 53,300 | 1.23 |
| 1d | 181.5 | 98 | 39,200 | 53,350 | 1.24 |
| 1d | 186.2 | 98 | 39,200 | 55,700 | 1.23 | a. As determined by $^1$H NMR spectroscopy, recorded in $d_6$-benzene.
b. SEC in DMF at room temperature, at a flow rate of 0.5 ml/min, with x2 PL Mixed-D columns, PL UV-1200, Optilab RI and DAWN EOS detectors.

In order to follow kinetics at short reaction times (and thus evaluate any effects of CTA structure on the pre-equilibrium in Scheme 1) a series of comparative polymerizations were monitored directly by NMR spectroscopy. CTA/I ratios of 5/1 were utilized with the temperature held constant at 60° C. in $d_6$-benzene. The spectra were obtained at 15-minute intervals for nine hours, with a data acquisition time of 108 seconds. Conversions at longer time intervals were followed by analyzing aliquots of identical solutions taken from separate flame-sealed ampoules heated in a water bath at 60° C. Polydispersities and absolute molecular weights were determined by size exclusion chromatography in DMF utilizing inline RI, UV and MALLS detectors.

FIG. 2 illustrates the respective kinetic plots for the polymerization of DMA with CTAs 1a–1d. The importance of reinitiation following fragmentation in the pre-equilibrium was demonstrated by the notable time intervals required to reach a constant slope in the respective $\ln(M_o/M_1)$ vs. time plots. These times were approximately 25 minutes for the novel CTAs 1c and 1d, compared to approximately 80 and 100 minutes for 1a and 1b respectively. This order was in agreement with that expected for reinitiation based on radical reactivity alone. The more stable, bulky cumyl radical from 1b should add to DMA slower than the primary benzyl radical from 1a and significantly slower than the acetadmido radicals from 1c and 1d. This was also consistent with the published reactivity ratios $r_1$ and $r_2$ for the styrene/DMA pair of 1.37 and 0.49 respectively.

In any event, once the pre-equilibrium phase of the RAFT process was reached, polymerizations with all four CTAs exhibited a $1^{st}$ order relationship between monomer conversion and polymerization time, at least up to moderately long polymerization times (FIG. 2). This first order relationship was maintained in the respective systems up to approximately 55% conversion, after which the rates decreased. The breakdown in "livingness" of these polymerizations, like other controlled free radical processes, was indicative of bimolecular termination events. These events were greatly suppressed by increasing the CTA/I ratio.

The theoretical molecular weights ($Mn_{Th}$) for the polymerizations at CTA/I ratios of 5/1 ranging from 14 to 186 hours are listed in Table 2. The $Mn_{Th}$ values, which were determined using Equation 1, are shown along with the experimentally determined molecular weights ($Mn_{SEC}$).

$$MW_{Th} = \left[\frac{[M] \times MW_{monomer}}{[CTA]}\right] \times \% \text{ Conversion} + MW_{CTA} \quad (1)$$

It was seen that the latter diverged dramatically from the former with conversion. When comparing the four CTAs at specific reaction time, the best correlation between the $Mn_{SEC}$ and the $Mn_{Th}$ was observed with 1c. This result was indicative of the importance of the events that took place early in the RAFT mechanism. The similarity between 1c and the monomer allowed all chains to be started early in the RAFT polymerization. For CTAs 1a and 1b, the differences between $Mn_{Th}$ and $Mn_{SEC}$ were slightly higher. This result was again consistent with those reported by Moad, G.; Chiefari, J.; Chong, Y. K.; Krstina, J.; Mayadunne, R. T. A.; Postma, A.; Rizzardo, E.; Thang, S. H. *Polym. Int.* 2000, 49, 993, for the polymerization of styrene with 1b.

Table 2 indicates that the conversion rates at extended time decreased dramatically due to a reduction in the number of active chains and the low concentration of monomer. Chromatograms, see FIGS. 3B–3D, from the DMA polymerizations using CTAs 1b–1d show evidence of bimolecular radical coupling as determined by the presence of high molecular weight shoulders. Using a MALLS detector it was determined that these shoulders have molecular weight values approximately twice that of the main peaks. In addition, the relative amounts of the high molecular weight impurities increased with increasing conversion. Although not quantified, it appears that PDMA synthesized using 1b–1d contained approximately similar numbers of dead chains, see FIG. 3B–D. These side reactions can be avoided simply by limiting the conversion to less than 50% or by increasing the CTA/I ratio.

Example 6

RAFT Polymerization of N,N-Dimethylacrylamide in Water

DMA homopolymers were synthesized in water via RAFT. Both sodium 4-cyanopentanoic acid dithiobenzoate (CTPNa) and N,N-dimethyl-s-thiobenzoylthiopropionamide (TBP) were employed as the RAFT chain transfer agents (CTAs). CTPNa was chosen due to its inherent water-solubility and its ability to mediate the controlled polymerization of anionic acrylamido monomers in aqueous media, while TBP was selected since the effectiveness of this CTA for the polymerization of DMA in organic media has recently been demonstrated. 4,4'-Azobis(4-cyanopentanoic acid) (V-501) was utilized as the free radical initiator in all instances, with the CTA/I ratio held constant at 5/1 ([Monomer]=1.83 M, [V-501]=9.2×10$^{-4}$ M, [CTA]=4.57×10$^{-3}$ M). The CTA/monomer ratios were chosen such that the theoretical $M_n$ at 100% conversion would be 40,000. The polymerization solutions were purged for 30 min with nitrogen to remove oxygen. The solutions were then transferred via cannula to individual rubber septa-sealed, glass test-tubes which were pre-purged with nitrogen. The test-tubes were immersed in a pre-heated water-bath at three different temperatures: 60, 70 and 80° C. The test tubes were removed from the water baths after various time intervals. Polymerizations were allowed to proceed for a total of 9.5 h. After removal from the water bath, the samples were immediately cooled in ice water and stored in a freezer until analysis.

The samples were analyzed by NMR spectroscopy (using a water-suppression technique) to determine conversion. A portion of each sample was diluted, and analyzed by aqueous size exclusion chromatography (ASEC) (using an eluent of 20% acetonitrile/80% 0.05 M $Na_2SO_4$, a Viscotek TSK Viscogel (4000PWxL) column, and Polymer Labs LC 1200 UV/V is, Wyatt Optilab DSP Interferometric refractometer, and Wyatt DAWN EOS multi angle laser light scattering detectors). The dn/dc of PDMA in the above eluent was determined to be 0.1645 at 25° C. The molecular weight and polydispersity data were determined using the Wyatt ASTRA SEC/LS software package.

Figure 4:
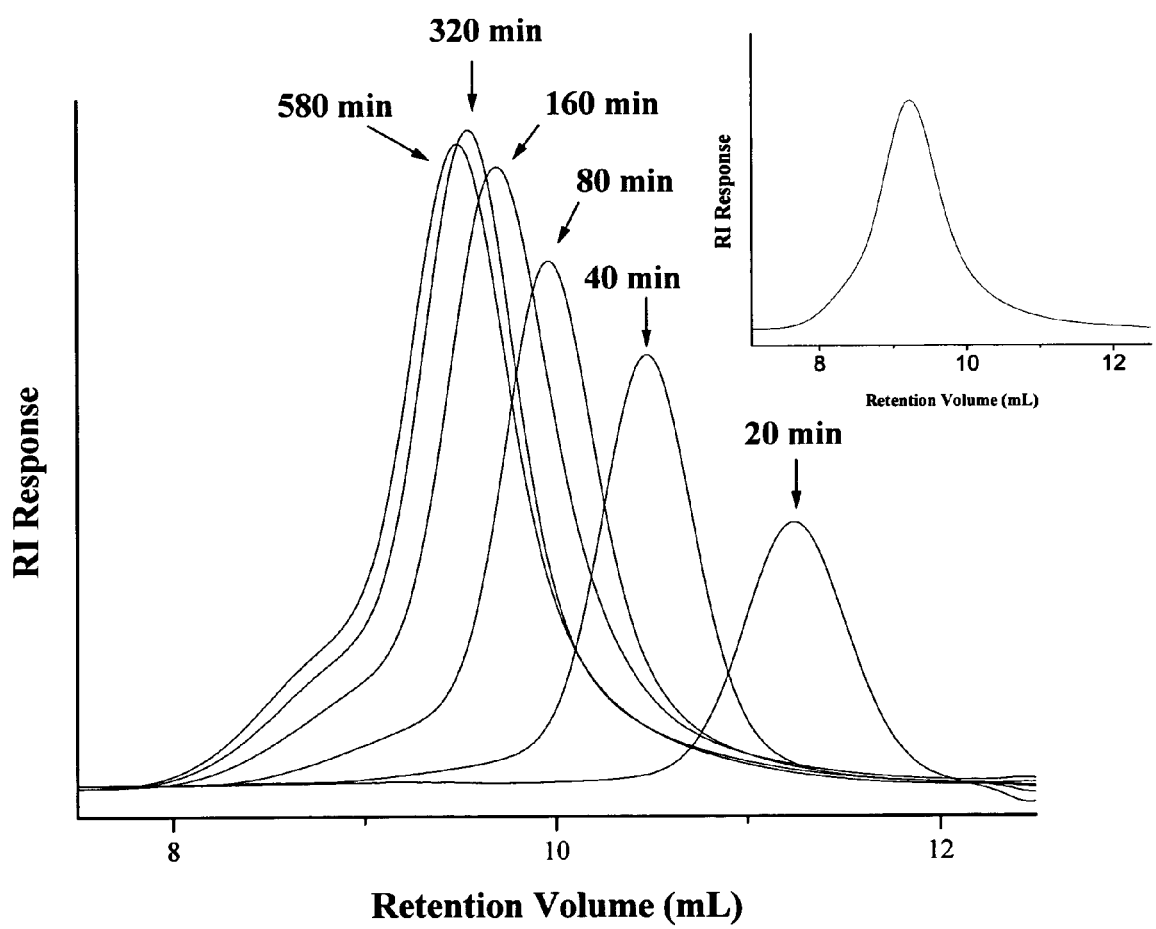
FIG. 4 shows aqueous SEC for poly(DMA) synthesized in the presence of sodium 4-cyanopentanoic acid dithiobenzoate (CTPNa) in water at 80° C. The insert shows poly(DMA) synthesized under identical conditions in the presence of TBP.

FIG. 4 shows an example of the evolution of molecular weight, as determined by ASEC on direct aliquots from the PDMA homopolymer synthesized using CTPNa at 80° C. An increase in the molecular weight (peak shifts to shorter retention times) was observed which was, at least qualitatively, indicative of a controlled polymerization. There is evidence in the chromatograms, at T>160 min, of a small amount of high molecular weight species arising from uncontrolled polymerization or termination events (high molecular weight shoulder). This was not observed in chromatograms of the TBP-mediated polymerization at the same temperature (see insert).

Figure 5:
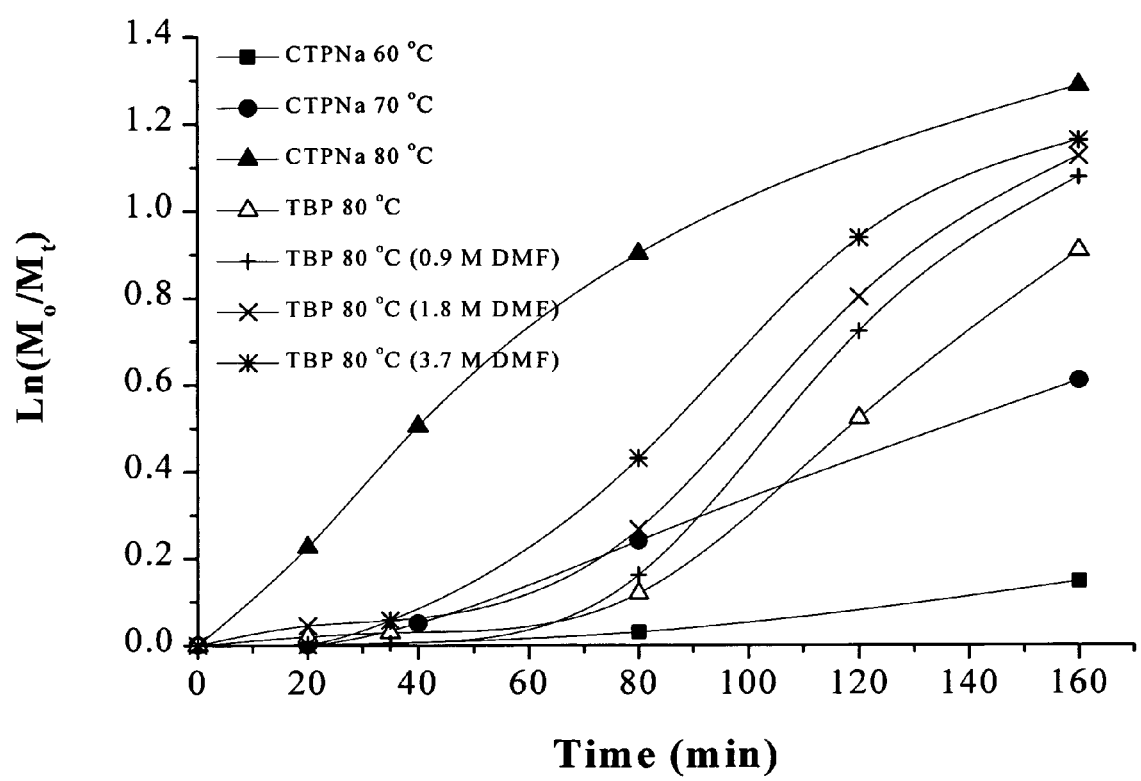
FIG. 5 shows kinetic plots for the polymerization of DMA in the presence of CTPNa at 60° C., 70° C., and 80° C. and in the presence of TBP at 80° C. for concentrations of 0.0 M, 0.9 M, 1.8 M, and 3.7 M DMF in $H_2O$.

The kinetic plots for the CTPNa and TBP-mediated polymerizations of DMA utilizing the 5/1 ratio of CTA/I are shown in FIG. 5. The CTPNa-mediated polymerizations (solid symbols) showed the expected increases in rate with increasing temperature. Successful polymerization in the presence of TBP (open triangle) in water occurred only at the higher temperature of 80° C. with much lower rates of monomer incorporation at 60 and 70° C. (data not shown).

Figure 6:
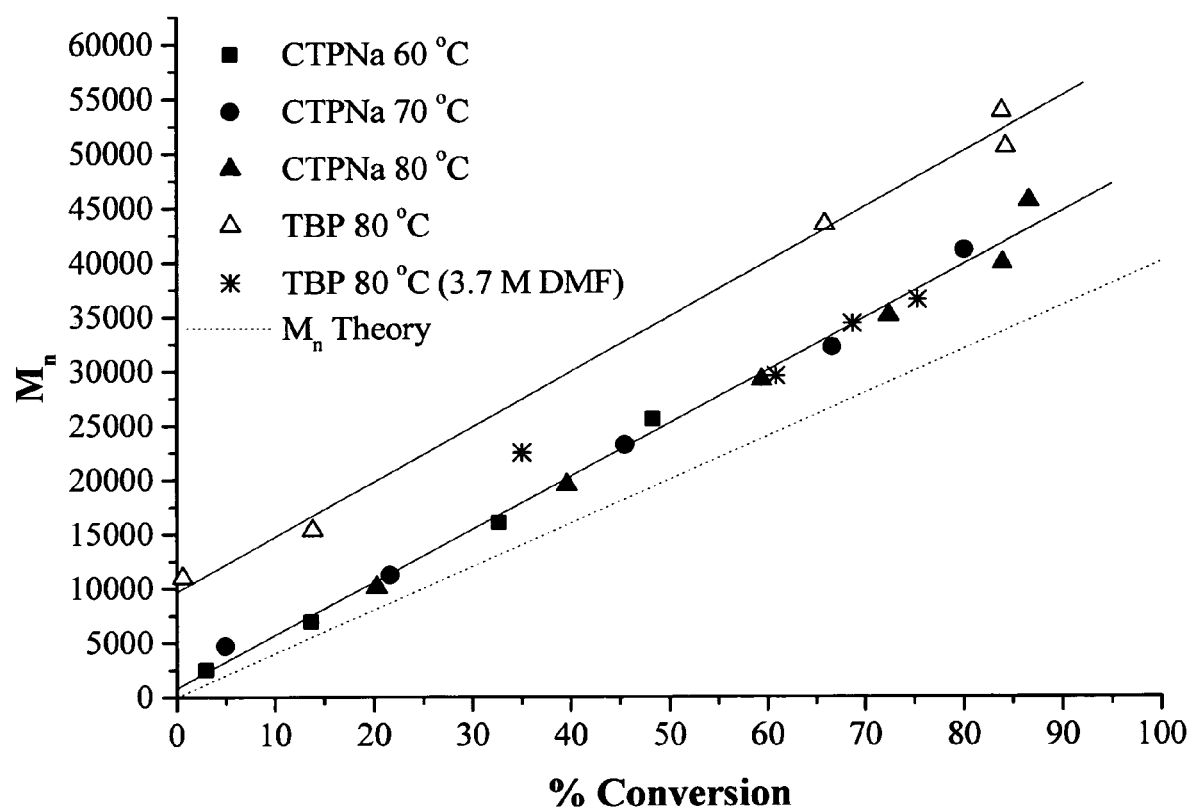
FIG. 6 shows plots of molecular weight versus concentration for poly(DMA) synthesized at 60° C., 70° C., and 80° C. in the presence of CTPNa, at 80° C. in the presence of N,N-dimethyl-s-thiobenzoylthiopropionamide (TBP), at at 80° C. in 3.7 M DMF in $H_2O$ in the presence of TBP.

The molecular weight versus conversion data for the CTPNa and TBP-mediated polymerizations of DMA are shown in FIG. 6. The plots in water alone for TBP at 80° C. and CTPNa at 60, 70 and 80° C., respectively, are linear and exhibit identical slopes, though the former has a non-zero intercept. Addition of sufficient quantities of DMF to the aqueous solutions during polymerization resulted in a remarkably linear relationship between experimentally determined molecular weight and conversion for CTPNa and TBP mediated polymerizations. This can be compared to the theoretical projection of molecular weight versus conversion (dotted line in FIG. 6) of an ideal RAFT polymerization. Controlled chain growth was realized at all three temperatures with CTPNa and at 80° C. with TBP. Molecular weights were somewhat higher than theoretically predicted possibly due to underlying non-RAFT polymerization and/or radical coupling inherent to CRP processes. Addition of DMF to aqueous solutions of TBP results in better molecular weight control (Table 3). It is also clear from Table 3 that $M_w/M_n$ values ranging from 1.11 to 1.23 are well within the limits considered for controlled polymerizations.

TABLE 3

| CTA | Temp (° C.) | Time (min) | Conversion (%)[a] | $M_n$ Theory[b] | $M_n$ Expt[c] | $M_w/M_n$[c] |
|---|---|---|---|---|---|---|
| TBP | 60 | 580 | 1 | 400 | 7,400 | 1.67 |
| TBP | 70 | 580 | 25 | 10,000 | 30,600 | 1.17 |
| TBP | 80 | 160 | 66 | 26,400 | 43,500 | 1.14 |
| TBP (0.9 M DMF) | 80 | 160 | 66 | 26,400 | 39,300 | 1.14 |
| TBP (1.8 M DMF) | 80 | 160 | 68 | 27,200 | 34,700 | 1.23 |
| TBP (3.6 M DMF) | 80 | 160 | 69 | 27,600 | 34,400 | 1.20 |
| CTPNa | 60 | 160 | 48 | 19,200 | 25,560 | 1.11 |
| CTPNa | 70 | 160 | 80 | 32,000 | 41,130 | 1.15 |
| CTPNa | 80 | 160 | 87 | 34,800 | 45,570 | 1.14 |

[a]As determined by NMR spectroscopy.
[b]$Mn_{theory} = \{([M] \times MW_{mon})/[CTA]) \times \%Conversion\} + MW_{CTA}$.
[c]As determined by ASEC in 20% MeCN/80% 0.05 M $Na_2SO_4$ employing RI and light scattering detectors.

Example 7

Synthesis of dithiobenzoic acid, 2-(2-pyridinyl)ethyl ester

The crude product of newly synthesized dithiobenzoic acid (0.5 mol theoretically) was dissolved in benzene and placed in a round bottom flask equipped with a vigreaux column and magnetic stirbar. The reaction vessel was purged with nitrogen for 1 hour. Freshly distilled 2-vinylpyridine was added via syringe (43 ml, 0.4 mol) at 0° C. The reaction was then heated to reflux and allowed to react overnight. The viscous liquid that remained after the solvent was removed was then purified by column chromatography with neutral alumina as the stationary phase and 3/2 v/v methylene chloride/hexane as the mobile phase. The solvent was then removed from the red-orange fraction in vacuo and diethylether was added to the remaining liquid resulting in the precipitation of a slightly yellow solid. The liquid phase was retained and after solvent removal in vacuo the desired product was obtained as an red-orange liquid. Structure was confirmed by from $^1$H, $^{13}$C, and $^{13}$C DEPT N.M.R. spectroscopy.

Example 8

Synthesis of dithiophenylacetic acid, 2-(2-pyridinyl)ethyl ester

The crude product of newly synthesized dithiophenyl acetic acid (10 g, 59 mmol theoretically), freshly distilled 2-vinylpyridine (6.25 g, 59 mmol), and 1 mol % toluene sulfonic acid were dissolved in benzene and placed in a round bottom flask equipped with a vigreaux column and magnetic stirbar. The reaction was then heated to reflux and allowed to react for 16 hours. The viscous liquid that remained after the solvent was removed was then purified by column chromatography (silica 2/1 v/v hexane/ethyl acetate). Yield=3.9 g. $^1$H NMR (CDCl$_3$) δ=3.042 (t, 2 H), δ=3.573 (t, 2 H), δ=4.233 (s, 2H) δ=6.968–7.476 (m, 8H), δ=8.467, (d, 1H). $^{13}$C NMR (CDCl$_3$) δ=35.627 (CH$_2$), δ=36.180 (CH$_2$), δ=58.323 (CH$_2$), δ=121.93 (CH), δ=123.383 (CH$_2$), δ=127.501 (CH), δ=128.818 (CH), δ=129.346 (CH), δ=137.272 (C), δ=149.668 (CH), δ=159.305 (C), δ=235.369 (C=S).

Example 9

Synthesis of carbonodithioic acid, O-ethyl S-(2-pyridinyl-methyl) ester 1.00 g (3.9 mmol) of 2-(bromomethyl)pyridine hydrobromide and 0.36 g (3.9 mmol) of O-ethyldithiocarbonic acid, potassium salt were combined in a 50 ml round bottom flask with 20 ml of 100% ethanol. The reaction vessel was sealed with a rubber septum and oxygen was removed by several freeze-pump-thaw cycles. The reaction mixture was then warmed to room temperature and allowed to stir under positive nitrogen pressure. A white precipitate was observed after the first few minutes of the reaction. The reaction was allowed to stir for an additional 20 hours. 20 mL of 0.5M aqueous sodium hydroxide was then added causing the reaction mixture to become homogenous and take on a red color. Extraction with hexane after addition of an additional 20 ml of the sodium hydroxide solution yielded a fluorescent yellow-green solution. Hexane was removed and the residue was passed over a silica column (ethyl acetate as the elluent). The final product appears as a yellow-green liquid and fluoresces blue when exposed to long wavelength ultraviolet light. Yield=0.342 g (39%). $^1$H NMR (CDCl$_3$) δ=1.212 (t, 3 H), δ=4.353 (s, 2 H), δ=4.47 (q, 2 H), δ=7.002 (t, 1 H), δ=7.234 (d, 1 H), δ=7.466 (t, 1 H), δ=8.377 (d, 1 H). $^{13}$C NMR (CDCl$_3$) δ=13.929, δ=42.135, δ=70.358, δ=122.494 (CH), δ=123.424 (CH), δ=136.777 (CH), δ=149.660 (CH), δ=156.152 (C), δ=213.730 (C=S).

Example 10

Synthesis of dithiodiphenylacetic acid, 2-(2-pyridinyl)ethyl ester

Dithiodiphenylacetic acid was dissolved in benzene in a round bottom flask equipped with a vigreaux column and magnetic stir bar. 2-Vinyl pyridine was then added via syringe under nitrogen at room temperature. The reaction mixture was then brought to reflux and reacted for 5 hours. The reaction was allowed to cool to room temperature and extracted with portions of aqueous HCl at 0° C. until the aqueous phase remained colorless. The aqueous phases, which appear green when acidic, were then combined and washed with diethyl ether. Finally diethyl ether and aqueous sodium hydroxide were added at 0° C. until the color of the mixture became orange (pH ~12). The basic aqueous phase was extracted with portions of diethyl ether until the organic phase remained colorless. The solvent was then removed from the combined organic phases in vacuo and the remaining dark orange oil was purified by column chromatography with silica gel (acetone) followed by a second purification by column chromatography (silica gel/dichloromethane). Evaporation of the solvent yielded the desired compound as a pale orange solid. $^1$H NMR (CDCl$_3$) δ=3.113 (t, 2 H), δ=3.654 (t, 2 H), δ=5.895 (s, 1 H), δ=7.074–8.535 (19 H). $^{13}$C NMR (CDCl$_3$) δ=35.336 (CH$_2$), δ=35.805 (CH$_2$), δ=70.746 (CH), δ=121.649 (CH), δ=123.133 (CH), δ=127.226 (CH), δ=128.300 (CH), δ=129.105 (CH), δ=136.427 (CH), δ=140.562 (C), δ=149.402 (CH), δ=159.089 (CH), δ=237.770 (C=S).

Example 11

Synthesis of Naphthyl Dithiocarbonylthio CTA 11.01 g (0.07003 mol) of methyl-2-mercaptopropionate was mixed with 12.29 g (0.07817 mol) naphthylmethylamine in a 50 mL 1 neck round bottom flask equipped with a magnetic stir bar. The flask was purged with nitrogen. The reaction was heated to 145° C. for 4 hours. The reaction was allowed to cool to room temperature and subjected to a full vacuum to remove the unreacted thiol methyl ester. Since the absence of thiol peaks upon $^1$H NMR analysis indicated disulfide formation, a reduction of the naphthyl thiol product in ethanol was performed using sodium borohydride. The reduction procedure is analogous to that used by D'amico. The product was dissolved in 210 mL of ethanol and heated to 70° C. under nitrogen. To this mixture, a solution of NaBH$_4$ (2.64 grams in 140 mL of ethanol) was added. The temperature was raised to 80° C. for one hour. The reaction was cooled to room temperature, and 1 L of ice was added. The pH was then lowered to 3 using concentrated HCl. The precipitated solid naphthyl thiol was collected using a Buchner funnel, washed with deionized water, and dried in a vacuum oven. The product was purified by recrystallization using a mixture of acetone and hexane to yield white crystals. Yield=61%. MP: 125 to 127° C.

10.00 g (0.04076 mol) of the Naphthylthiol and 26.12 g (0.1230 mol) of 2-(thiobenzoyl)thioglycolic acid were dissolved with a mixture of 350 mL of methylene chloride and 275 mL benzene. Once the reactants were dissolved, 100 mL of deionized H$_2$O was added. The contents were placed in a 1L 3 neck round bottom flask equipped with a stir bar. The reaction solution was purged with nitrogen for 30 min. The water was changed daily for one week. The water added was purged with nitrogen before addition. The organic phase was separated and the solvent was removed via a rotory evaporator to yield a pink solid. The compound was purified by recrystallization from a mixture of hexane and chloroform yielding a light pink solid. Yield=75.1%.

Example 12

Synthesis of Dansyl Dithiocarbonylthio CTA

N-(2-Aminoethyl)-5-(dimethylamino)-1-naphthalene-sulfonamide (2.51 g, 9.605 mmol) was mixed with of methyl-2-mercaptopropionate (1.86 g, 15.37 mmol) in a 50 mL 1 neck round bottom flask equipped with a magnetic stir bar. The reaction was heated to 145° C. and heated for 2 hours. The reaction was allowed to cool to room temperature and subjected to a full vacuum to remove the unreacted thiol methyl ester. The absence of thiol peaks upon $^1$H NMR analysis indicated disulfide formation, the product was reduced using NaBH$_4$ using the following procedure. To the crude product was added 17 mL of absolute EtOH in a 50 mL 1 neck round bottom flask. The solution was purged with nitrogen and heated to 80° C. NaBH$_4$ (0.4330 g) was mixed with 17 mL of EtOH and purged with nitrogen. The mixture was heated to 80° C. and slowly transferred into the dansyl solution. The solution was left to react for 1 hour, and allowed to cool to room temperature. To the reaction products 50 mL of ice was added. The mixture became cloudy and a yellow ppt formed on the glass. The pH of the solution was lowered to 3 and the solution became clear. The pH was raised to approximately 8.5, upon which the aqueous phase became cloudy again. The aqueous phase was extracted twice with 50 mL of chloroform using a 150 mL sep funnel. The chloroform was removed via rotary evaporator off leaving a yellow/green oil of the dansylamide thiol. Yield=96%.

The dansylamide thiol 4.18 g (0.03297 mol) was mixed with 40 mL of diethyl ether. S-(Thiobenzoyl)thioglycolic acid (7.00 g, 0.010 mol) was mixed with 50 mL of deionized H$_2$O and neutralized to a final pH of 7.5 using a dilute NaOH solution to a final volume of 100 mL. The two solutions were mixed in a 1 neck 150 mL round bottom flask with stir bar, yielding a two-phase mixture. The reaction vessel was kept in the dark and allowed to stir for one week. After one week, the ethereal phase had taken on a dark orange color. The ethereal phase was separated, washed twice with DIH$_2$O and dried with anhydrous sodium sulfate. The product was purified by column chromatography on silica gel in a mixed solvent system of acetone and methylene chloride (10:90). $^1$H NMR (d$_6$-DMSO) δ (ppm): 1.34 (m, CH$_2$—CH$_2$), 1.56 (m, CH), 2.76 (t, CH$_2$—NCO), 2.81 (s, —N(CH$_3$)$_2$), 2.94 (CH$_2$—NSO$_2$), 4.66 (s, CH$_3$), 7.23–8.44 (m, 11H ArH). $^{13}$C NMR (d$_6$-DMSO) δ (ppm): 17.5 (CH$_3$), 25.93 (CH$_2$), 26.65 (CH$_2$), 38.38 (CH$_2$), 42.12 (CH$_2$), 45.13 (—N(CH$_3$)$_2$), 50.59 (CH—S), 115.11–151.35 (16C, ArC), 169.21 (CO), 226.89 (CS).

Example 13

Synthesis of N,N'-Ethylenebis(s-thiobenzoylthio)propionamide

This reaction was performed as previously reported by Atkinson, E.; Richard, H.; Bruni, J.; Granchelli, F. *J. Med. Chem.* 1965 8(1), 29–33. Methyl-2-mercaptopropionate (33.77 g, 0.2858 mol) was mixed with 5.05 g of ethylenediamine (0.08402 mol) in a 50 mL 1 neck round bottom flask equipped with a magnetic stir bar. The vessel was purged with nitrogen. The reaction vessel was heated to 145° C. for three hours. The contents were subjected to a full vacuum for one hour to remove excess thiol. The melting point of the white solid product was determined to be between 190–192° C. Yield=99% of N,N-ethylenebis(2-mercaptopropionamide). The absence of thiol peaks upon $^1$H NMR analysis indicated polymeric disulfide formation. The product was reduced using an aqueous solution of 0.1 M NaOH and not purified further.

3.15 grams (0.01323 mol) of N,N'-ethylenebis(2-mercaptopropionamide) was mixed with 30 mL of deionized H$_2$O. The solid was not miscible with water. The pH of the solution was raised until the compound became soluble. The final pH was adjusted to 9.4 at a final volume of 100 mL. The solution was then purged with nitrogen and the pH was lowered to 7.4. The solution was purged a second time and the mixture was added directly to a solution of sodium s-(thiobenzoyl)thioglycolate [8.63 g, (40.65 mmol) of the acid neutralized to a pH of 7.5 to a total volume of 100 mL]. Immediately, the solution became a cloudy orange color. After a few minutes, a dark precipitate started to collect. The product was placed in a refrigerator for four days. The aqueous phase was a clear orange color. A dark precipitate was formed at the bottom of the flask. Filtering with a fritted glass funnel isolated a pink solid. The product was broken up using a mortar and pestle and dissolved with 150 mL of methanol. Water was added until the mixture just became cloudy. The solution was placed in the freezer overnight. The precipitated pink solid was collected via filtration and dried in a vacuum oven for three hours. The compound was purified by column chromatography on silca gel using a mixed solvent system of ethyl ether/methylene chloride (60:40). Yield=57.72% yield. M.P.=116–118° C. $^1$H NMR in CDCl$_3$ (TMS ref): 1.55 (d, —CH$_3$) 3.30 (s, —CH$_2$—N) 4.56 (m, —CH) 6.74 (s, —NH) 7.31, 7.48, 7.92 (m, CH). $^{13}$C NMR: 15.22 (CH$_3$) 38.85 (NH—CH2) 47.50 (CH) 126.13, 127.44, 132.07 (CH) 143.08 (C) 170.28 (C=O) 226.23 (CS$_2$).

Example 14

Preparation of Low polydispersity poly(N,N-dimethyl acrylamide) using N,N-Dimethyl-s-thiobenzoylthiopropionamide N,N-Dimethyl-s-thiobenzoylthiopropionamide (127.46 mg) was weighed into a 20 mL scintillation vial and N,N-dimethyl acrylamide (19.983 g) was added to the scintillation vial. The mixture was transferred to a 100 mL volumetric flask and made to the mark with distilled deionized water. A 4.8 mL aliquot of a stock solution of 4,4'-Azobis (4-cyanopentanoic acid) (2.01×10$^{-2}$ M) was added. This mixture was purged with nitrogen for 30 minutes and transferred via a cannula to pre-nitrogen purged test tubes, which were sealed with rubber septa. The test-tubes were immersed in a pre-heated water-bath at three different temperatures: 60, 70 and 80° C. The test tubes were removed from the water baths after various time intervals. Polymerizations were allowed to proceed for a total of 9.5 h. After removal from the water bath, the samples were immediately cooled in ice water and stored in a freezer until analysis.

| CTA | Temp (° C.) | Time (min) | Conversion (%)[a] | $M_n$ theory | $M_n$ Expt[b] | $M_w/M_n$[b] |
|-----|-------------|------------|-------------------|--------------|---------------|--------------|
| TBP | 60 | 580 | 1 | 400 | 7,400 | 1.67 |
| TBP | 70 | 580 | 25 | 10,000 | 30,600 | 1.17 |
| TBP | 80 | 580 | 84 | 33,600 | 53,780 | 1.15 |

[a]As determined by $^1$H NMR spectroscopy.
[b]As determined by ASEC in 20% MeCN/80% 0.05 M Na$_2$SO$_4$ employing RI and light scattering detectors.

Example 15

Preparation of Sodium 2-(2-thiobenzoylsulfonyl-propionylamino)-ethanesulfonate

Sodium 2-(2-bromopropionylamino)-ethanesulfonate 25.6 g of taurine (204 mmol) and 16.38 g of NaOH (409 mmol) were dissolved in 20 ml of deionized water. 2-Bromopropionyl bromide (44 g, 21.36 ml, 204 mmol) dissolved in 50 ml of dichloromethane was then added to the solution drop wise at 0° C. over 30 minutes. During the addition, a large amount of solid was produced. The reaction flask was manually agitated to thoroughly mix the compounds until no more exotherm was observed with additional agitation. The reaction mixture was then allowed to sit for 1 hour. The solid was filtered and washed with a small amount of absolute ethanol and then ethyl ether and then dried in vacuo. The compound can be used in this state or recrystallized from methanol.

Sodium 2-(2-thiobenzoylsulfonylpropionylamino)-ethanesulfonate (STPE)

Freshly synthesized dithiobenzoic acid, sodium salt (9.12 g) dissolved in 1 ml of water was combined with 8.5 g of crude sodium 2-(2-bromopropionylamino)-ethanesulfonate dissolved in 6 ml of water in a 20 ml vial. Immediately upon mixing a precipitate started to form accompanied by a strong exotherm. After 24 hours at room temperature, the solid was filtered and washed with a small amount of water. The liquid portion was precipitated into acetone to yield a pink solid that was isolated by centrifugation. The precipitate was extracted with acetone until the liquid phase was a pale orange color. The precipitate was dissolved in a minimum amount of water and recrystallized at 4° C. over several days. $^1$H NMR δ=1.22, 1.45 (2d, 3H), 2.92 (d, 3H), 3.44 (d, 3H), 4.35 (q, 1H), 7.29 (q, 2H), 7.44 (d, 1H), 7.76 (d, 2H). $^{13}$C NMR 15.77, 35.55, 49.59, 50.08, 126.81 (CH), 128.82 (CH), 133.39 (CH), 144.30 (C), 173.71 (C=O), 228.95 (C=S). Analysis for CHNS Calculated: C, 40.55%, H, 3.97%, N, 3.91%, S, 27.07%. Found: C, 37.85%, H, 3.37%, N, 3.58%, S, 25.26%.

Example 16

Polymerization of Acrylamide Using Sodium 2-(2-thiobenzoylsulfonylpropionylarnino)-ethanesulfonate (STPE)

2,2'-Azobis(2-methyl-N-(2-hydroxyethyl)-propionamide) (VA-086, Wako) was utilized as the free radical initiator and STPE as the chain transfer agent (CTA) with a CTA/I ratio of 1.15, an acrylamide concentration of 2.0 M, a VA-086 concentration of $2.17 \times 10^{-3}$ M, and a CTA concentration of $2.50 \times 10^{-3}$ M. The CTA/monomer ratio was chosen for a theoretical degree of polymerization of 800 at 100% conversion. Buffer solutions (pH=5.0) for polymerization contained 0.272 M acetic acid and 0.728 M sodium acetate. Solutions were placed in septa-sealed vials, purged for 30 minutes with $N_2$, and heated to 70° C. with agitation. Aliquots were removed after 0, 2, 4, 8, 12, and 24 hours. A portion of each aliquot was diluted and analyzed by aqueous size exclusion chromatography (ASEC) using an eluent of 20% acetonitrile/80% 0.05 M $Na_2SO_4$, Viscotek TSK Viscogel coluimn, Polymer Labs LC 1200 UV/vis, Wyatt Optilab DSP Interferometric refractometer, and Wyatt DAWN EOS multiangle laser light scattering detectors. Conversions were determined by comparing the area of the UV signal corresponding to monomer at t=0 to the area at $t_x$. The dn/dc of polyacrylamide in the above eluent was previously determined to be 0.160 at 25° C. Absolute molecular weights and polydispersities were determined using the Wyatt ASTRA SEC/LS software package.

Chain extension of polyacrylamide was carried out as above but STPE was replaced by a polyacrylamide macro-CTA (molecular weight of 20300, polydispersity index (PDI) of 1.03) such that the CTA/monomer ratio and the CTA/initiator was the same.

Figure 7:
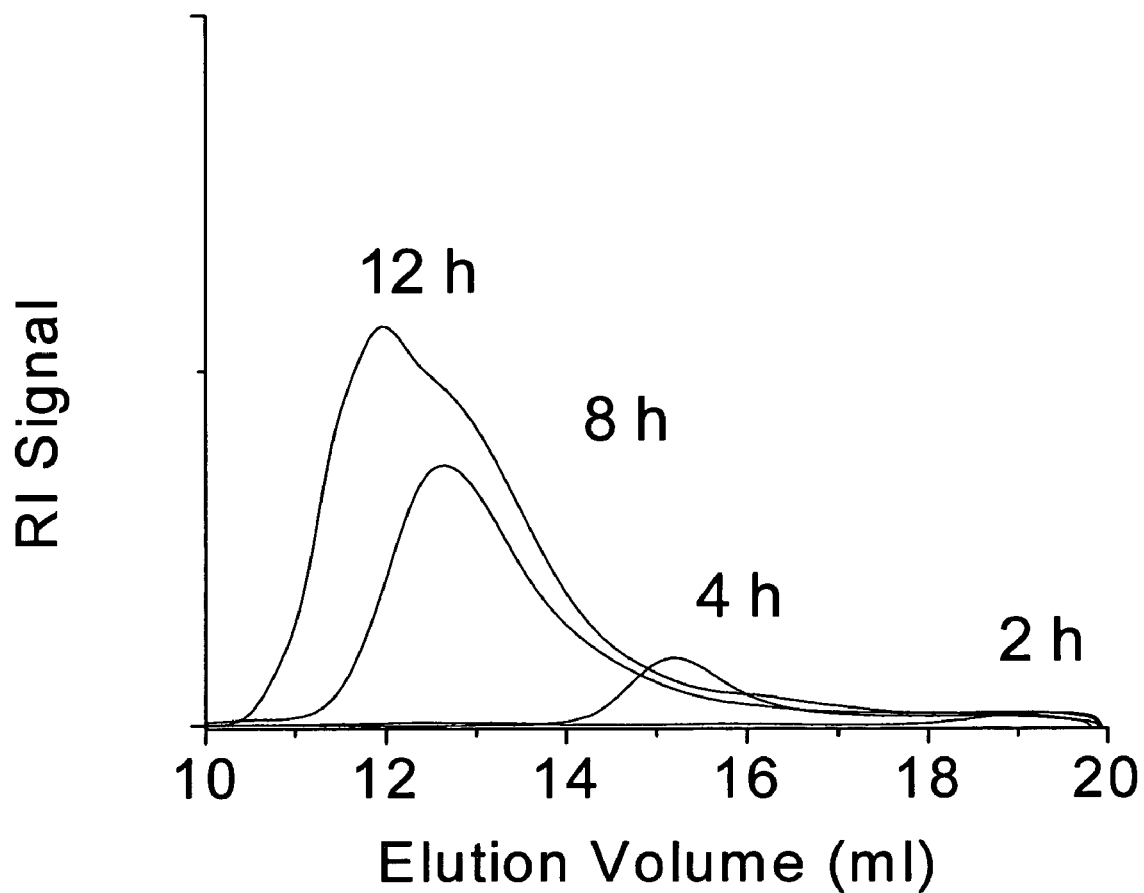
FIG. 7 shows typical results for the polymerization of acrylamide in the presence of a dithioester under ambient pH conditions. At 2 hours, no polymer was observed; at 4 hours, all color bleached from the reaction medium and the polymer had a mean molecular weight of 24,900 and a polydispersity index (PDI) of 1.09; at 8 hours, the polymer had a mean molecular weight of 114,000 and a PDI of 1.87; at 12 hours, the polymer had a mean molecular weight of 239,000 and a PDI of 2.98.
Figure 8A:
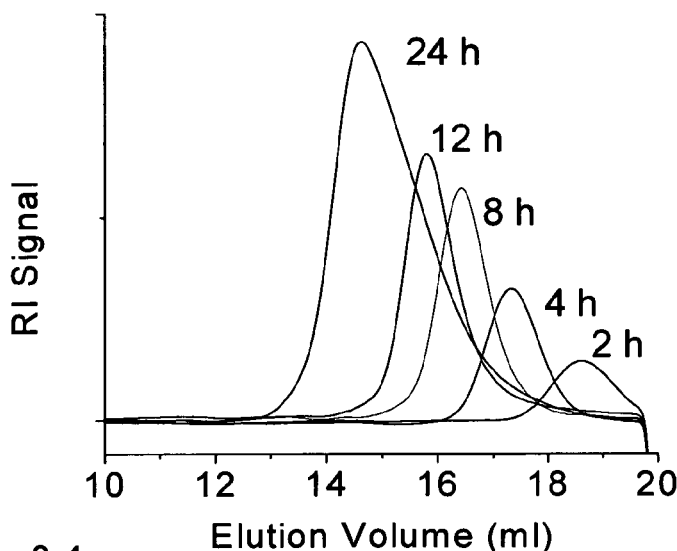
FIG. 8A shows ASEC chromatographs (RI traces) for the polymerization of acrylamide in an acetic acid/sodium acetate buffer showing the evolution of molecular weight with time.
Figure 8B:
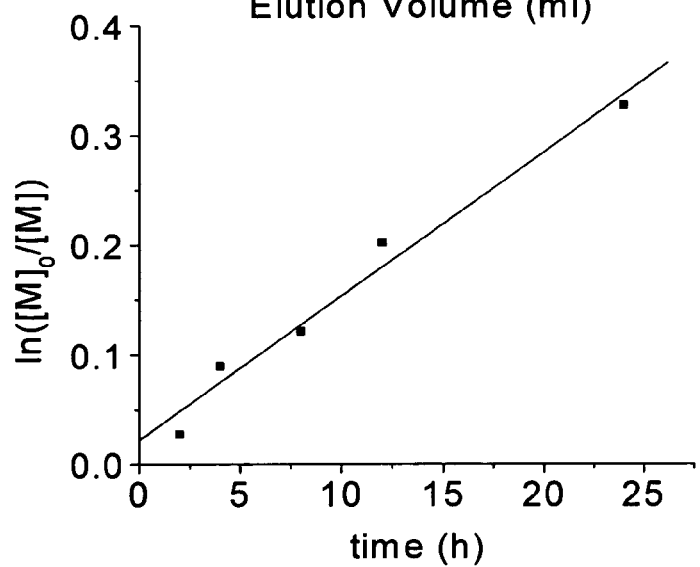
FIG. 8B shows a first order rate plot for the polymerization of acrylamide in an acetic acid/sodium acetate buffer.
Figure 8C:
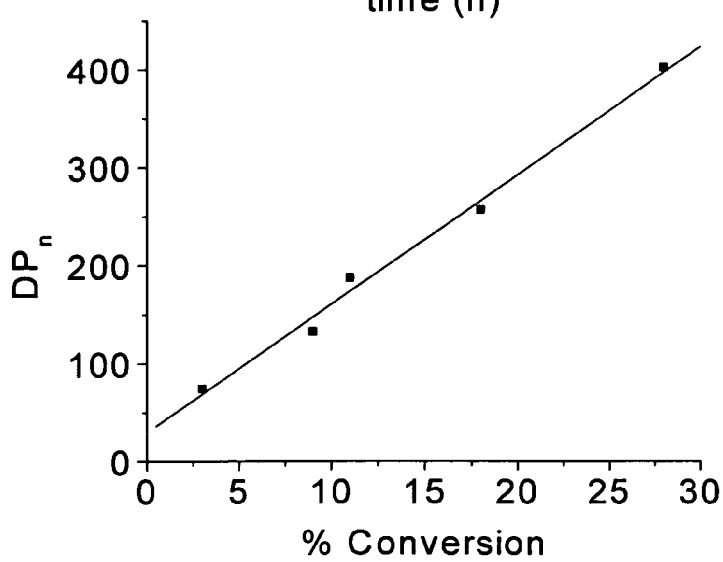
FIG. 8C show the plot of degree of polymerization $DP_n$ versus conversion for the polymerization of acrylamide in an acetic aicd/sodium acetate buffer.

The polymerization of acrylamide in water at intermediate pH's produces results typified by FIG. 7. In these polymerizations at pH=7 no polymer is observed for several hours during which the color is slowly bleached from the polymerization solution. Only after all the color is gone, indicating complete loss of the dithioester moiety, is polymer observed. The very high molecular weights and broad polydispersities are characteristic of uncontrolled acrylamide polymerization. FIGS. 8A–8C and Table 4, however, clearly demonstrate much better control of the polymerization process simply by performing the polymerization in an acetic acid/sodium acetate buffer (pH=5.0). Under these conditions the evolution of molecular weight was clearly observed as peaks shifted to shorter retention times in ASEC FIG. 8A). Further, the first order rate plot (FIG. 8B) and the plot of $DP_n$ vs conversion FIG. 8C) are both linear indicating controlled polymerization. Polydispersities were generally very low decreasing from 1.15 to between 1.04 and 1.06 at intermediate reaction times. At very long reaction times the polydispersity increased to 1.26, remaining well below the theoretical limit of 1.5 for conventional free radical polymerization.

TABLE 4

| Polymerization Time (h) | % Conversion[a] | $M_n$ (g/mol)[a] | $M_n$, theoretical (g/mol)[b] | PDI[a] |
|---|---|---|---|---|
| 0 | 0 | — | — | — |
| 2 | 3 | 5300 | 1710 | 1.15 |
| 4 | 9 | 9790 | 5120 | 1.05 |
| 8 | 11 | 13700 | 6260 | 1.04 |
| 12 | 18 | 18600 | 10200 | 1.06 |
| 24 | 28 | 28900 | 15900 | 1.26 |

[a]determined by ASEC
[b]calculated from conversion

Figure 9:
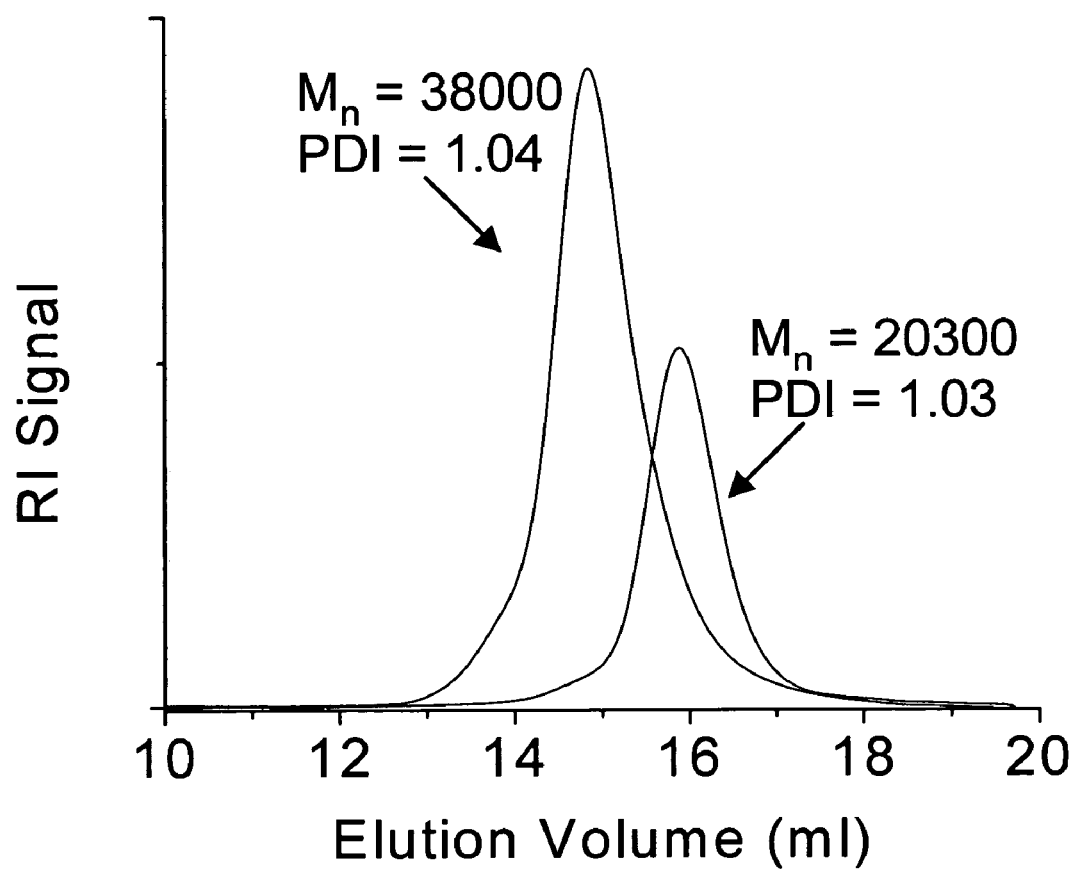
FIG. 9 shows ASEC chromatographs (RI traces) for the polymerization of acrylamide in an acetic acid/sodium acetate buffer using a polyacrylamide macro-CTA as the chain transfer agent and showing the evolution of molecular weight.

In order to further demonstrate the "livingness" of acrylamide polymerization under these conditions, a polyacrylamide macro-CTA was prepared ($M_n=2.03 \times 10^4$, PDI=1.03), isolated by dialysis and lyophilized to yield an orange powder. A polymerization solution was then prepared as before and this macro-CTA was used to extend the polyacrylamide chain. FIG. 9 demonstrates that chain extension occurs with essentially quantitative blocking efficiency, indicating nearly all of the macro-CTA chain ends were active. A final 50/50 composition was targeted for the first and extended segments (blocks). ASEC analysis indicated $2.03 \times 10^4$ g mol$^{-1}$ and $1.8 \times 10^4$ g mol$^{-1}$ for the respective segments, proving targeted molecular weights may be achieved. Interestingly, the molecular weights for all the polymers synthesized were substantially higher than the predicted theoretical molecular weights. This has also been observed for other neutral acrylamido monomers polymerized in the presence of a dithioester compound.

While not being bound by theory, it is believed that the marked difference in polymerization behavior of acrylamide under ambient and buffered conditions is related to the extent of CTA degradation byproducts generated during monomer hydrolysis. Even a low percentage of acrylamide hydrolysis can produce enough ammonia to convert all dithioesters in solution to a thiol and thiobenzamide (at a molar ratio of monomer to CTA of 800 only 0.125% of the monomer needs to hydrolyze to quantitatively react with the CTA). Under low pH conditions, however, ally ammonia produced via monomer hydrolysis would be effectively scavenged by the large excess of acid, thus greatly retarding nucleophilic attack on the dithioester. Examples shown above eliminate an alternative possibility of direct CTA hydrolysis at neutral pH by demonstrating that RAFT proceeds well in water for many monomers. Also, complete CTA hydrolysis at 70° C. requires days, in marked contrast to the hours observed in the case of acrylamide.

In conclusion, conditions allowing excellent control of the RAFT polymerization of acrylamide have been shown. The degree of control is illustrated in FIGS. 7 and 8A–C and Table 4 by the first order kinetic plot, the GPC curves showing the evolution of molecular weight with conversion, the resulting DP vs. conversion relationship and the narrow PDI values. Nearly quantitative chain extension and the low PDI value demonstrate the maintenance of dithioester end groups during polymerization. It is apparent that the macro-CTA's prepared under these conditions or those similar to the ones reported here will allow synthesis of block copolymers and other complex polymer architectures containing polyacrylamide subunits.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of preparing a polymer or copolymer comprising alkylacrylamide or acrylamide repeat units, comprising reacting:
   a) a dithioester or trithioester represented by the structural formula:

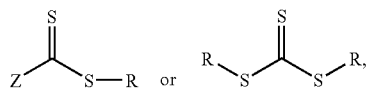

wherein:
   Z comprises an alkoxy group, a group represented by the structural formula:

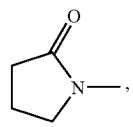

or one or more aromatic or heteroaromatic groups optionally substituted by one or more hydrophilic functional groups wherein optionally there is an ether or alkylene linkage between the aromatic or heteroaromatic group and the dithioester moiety; and
   R comprises a group represented by the structural formula:

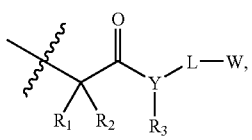

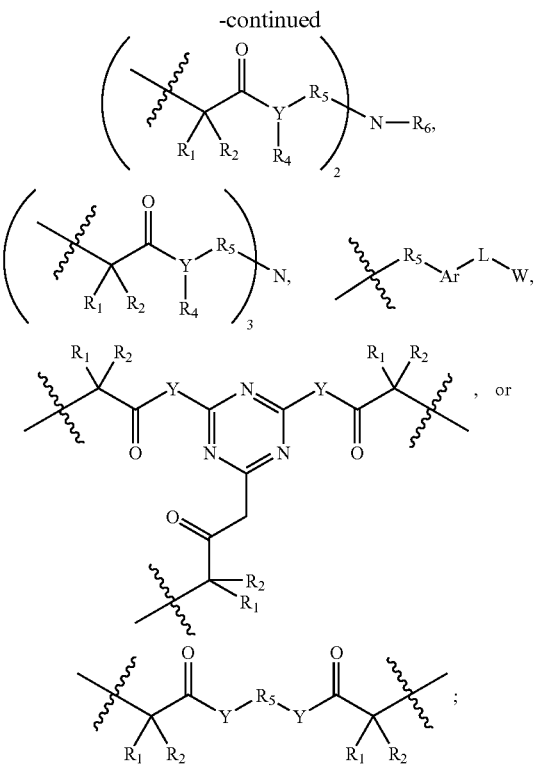

wherein:
   Ar is an aromatic or heteroaromatic group;
   L is a bond, an C1–C20 azaalkylene group, or a C1–C20 straight-chained or branched alkylene group;
   $R_1$ and $R_2$ are each independently hydrogen, a C1–C10 alkyl group, or a cyano group;
   $R_3$ and $R_4$ are each independently hydrogen or a C1–C10 alkyl group when Y is N or C, and are each lone electron pairs when Y is O;
   $R_5$ is a bond or a branched or straight-chained C1–C10 alkylene group;
   $R_6$ is hydrogen or a C1–C10 alkyl group;
   W is selected from the group consisting of —H, —SO$_3$$^-$M$^+$, —COOH, —COO$^-$M$^+$, —NH$_2$, —NR'$_2$, —NR'H, —NR'$_3$$^+$X$^-$, PO$_4$$^-$M$^+$, —OH, —(—OCH$_2$CH$_2$—)$_x$R', —(—CH$_2$CH$_2$O—)$_x$R', —CONH$_2$, —CONHR', —CONR'$_2$, —NR'(CH$_2$)$_x$COO$^-$M$^+$, —NR'(CH$_2$)$_x$OPO$_3$$^-$M$^+$, —NR'(CH$_2$)$_x$SO$_3$$^-$M$^+$, —N$^+$R'$_2$(CH$_2$)$_x$COO$^-$M$^+$, —N$^+$R'$_2$(CH$_2$)$_x$OPO$_3$$^-$M$^+$, —N$^+$R'$_2$(CH$_2$)$_x$SO$_3$$^-$M$^+$, —SCN, naphthyl, and dansyl;
   M$^+$ is ammonia, an ammonium ion, an alkali metal ion, an alkaline earth metal ion, or hydronium;
   R' is independently hydrogen or an alkyl group;
   x is an integer from 1 to about 20;
   X$^-$ is a halide, sulfate, phosphate, carboxylate, or sulfonate; and
   Y is selected from the group consisting of N, O, and C;
   b) a polymerizable monomer or co-monomer selected from the group consisting of alkylacrylamides and acrylamides; and
   c) free radicals produced by a free radical source in an aqueous or primarily aqueous buffer solution having a pH greater than about 2 and less than about 6.5.

2. The method of claim 1, wherein the polymerizable monomer or co-monomer is acrylamide.

3. The method of claim 2, wherein the aqueous or primarily aqueous buffer solution has a pH greater than about 4 and less than about 6.

4. The method of claim 2, wherein $R_1$ and $R_2$ are each independently hydrogen or a methyl group.

5. The method of claim 4, wherein Z comprises a phenyl, benzyl, pyrrole, indole, isoindole, or ethoxy group.

6. The method of claim 5, wherein R is represented by a structural formula selected from the group consisting of:

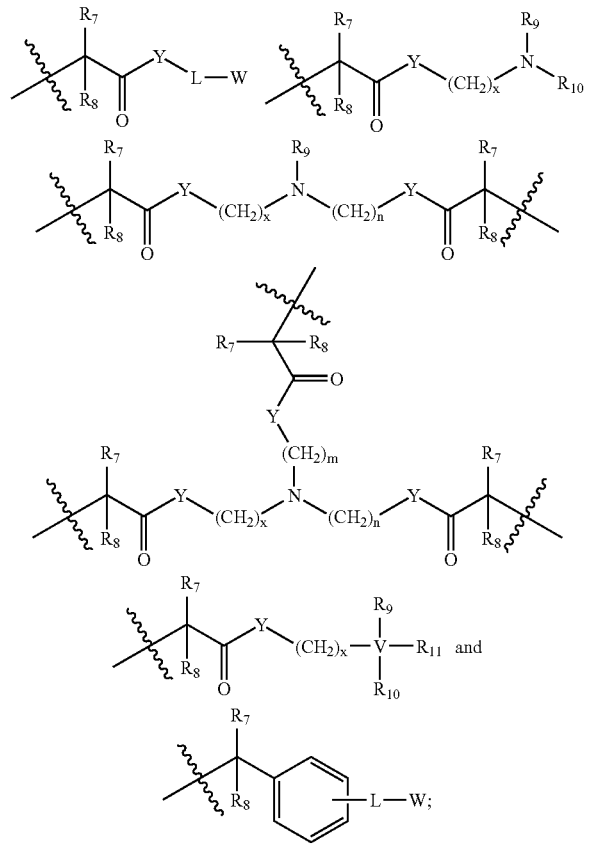

m and n are each integers from 1 to about 10;

$R_7$, $R_8$, $R_9$, $R_{10}$, and $R_{11}$ are each independently hydrogen or a C1–C10 alkyl group;

L, $M^+$, R', W, $X^-$, x, and Y are as defined above; and

V is selected from the group consisting of C and N.

7. The method of claim 6, wherein $R_7$ and $R_8$ are each independently hydrogen or a methyl group.

8. The method of claim 7, wherein Z comprises a phenyl, benzyl, pyrrole, indole, or isoindole group.

9. The method of claim 8, wherein Z is represented by a structural formula selected the group consisting of:

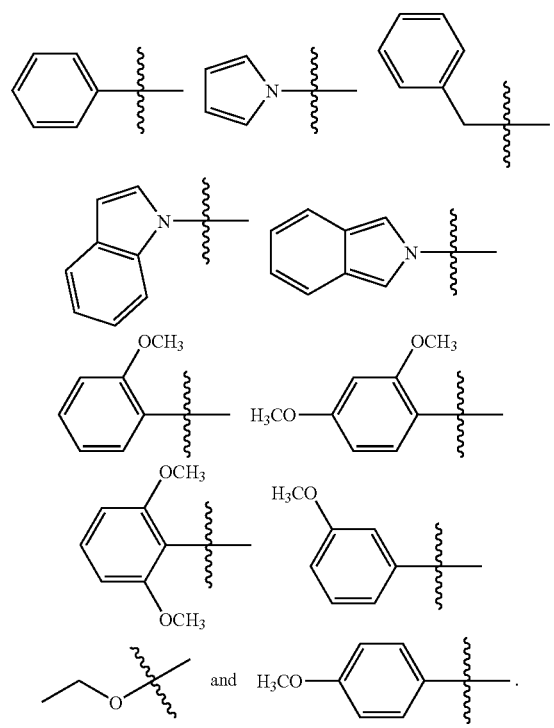

10. The method of claim 1, wherein the aqueous or primarily aqueous buffer solution has a pH greater than about 4.5 and less than about 5.5.

* * * * *